(12) United States Patent
Hu et al.

(10) Patent No.: US 9,549,965 B2
(45) Date of Patent: Jan. 24, 2017

(54) PHARMACEUTICAL COMPOSITION FOR TREATING A MICROBIAL INFECTION

(71) Applicant: HELPERBY THERAPEUTICS LIMITED, London (GB)

(72) Inventors: Yanmin Hu, London (GB); Anthony R M Coates, London (GB)

(73) Assignee: Helperby Therapeutics Limited, London (GB)

( * ) Notice: Subject to any disclaimer, the term of this patent is extended or adjusted under 35 U.S.C. 154(b) by 0 days.

(21) Appl. No.: 14/862,108

(22) Filed: Sep. 22, 2015

(65) Prior Publication Data
US 2016/0082073 A1   Mar. 24, 2016

Related U.S. Application Data

(63) Continuation of application No. 13/821,448, filed as application No. PCT/GB2011/051695 on Sep. 9, 2011.

(30) Foreign Application Priority Data

Sep. 10, 2010   (GB) .................................. 1015079.5

(51) Int. Cl.
| | | |
|---|---|---|
| A61K 38/12 | (2006.01) | |
| A61K 31/138 | (2006.01) | |
| A61K 31/18 | (2006.01) | |
| A61K 31/395 | (2006.01) | |
| A61K 31/417 | (2006.01) | |
| A61K 31/475 | (2006.01) | |
| A61K 31/517 | (2006.01) | |
| A61K 45/06 | (2006.01) | |
| A61K 31/05 | (2006.01) | |
| A61K 31/10 | (2006.01) | |
| A61K 31/167 | (2006.01) | |
| A61K 31/216 | (2006.01) | |
| A61K 31/282 | (2006.01) | |
| A61K 31/305 | (2006.01) | |
| A61K 31/382 | (2006.01) | |
| A61K 31/407 | (2006.01) | |
| A61K 31/4178 | (2006.01) | |
| A61K 31/445 | (2006.01) | |
| A61K 31/4709 | (2006.01) | |
| A61K 31/473 | (2006.01) | |
| A61K 31/4741 | (2006.01) | |
| A61K 31/5415 | (2006.01) | |
| A61K 31/704 | (2006.01) | |
| A61K 31/7052 | (2006.01) | |
| A61K 33/24 | (2006.01) | |
| A61K 38/14 | (2006.01) | |
| A61K 31/145 | (2006.01) | |

(52) U.S. Cl.
CPC ............... *A61K 38/12* (2013.01); *A61K 31/05* (2013.01); *A61K 31/10* (2013.01); *A61K 31/138* (2013.01); *A61K 31/145* (2013.01); *A61K 31/167* (2013.01); *A61K 31/18* (2013.01); *A61K 31/216* (2013.01); *A61K 31/282* (2013.01); *A61K 31/305* (2013.01); *A61K 31/382* (2013.01); *A61K 31/395* (2013.01); *A61K 31/407* (2013.01); *A61K 31/417* (2013.01); *A61K 31/4178* (2013.01); *A61K 31/445* (2013.01); *A61K 31/473* (2013.01); *A61K 31/475* (2013.01); *A61K 31/4709* (2013.01); *A61K 31/4741* (2013.01); *A61K 31/517* (2013.01); *A61K 31/5415* (2013.01); *A61K 31/704* (2013.01); *A61K 31/7052* (2013.01); *A61K 33/24* (2013.01); *A61K 38/14* (2013.01); *A61K 45/06* (2013.01)

(58) Field of Classification Search
CPC ... A61K 38/12; A61K 31/138; A61K 2300/00
See application file for complete search history.

(56) References Cited

U.S. PATENT DOCUMENTS

| | | | | |
|---|---|---|---|---|
| 5,290,774 A | * | 3/1994 | Morita ................. | A61K 9/0048 514/218 |
| 2003/0229082 A1 | | 12/2003 | James et al. | |
| 2008/0113031 A1 | * | 5/2008 | Moodley .............. | A61K 9/5073 424/490 |
| 2009/0131342 A1 | * | 5/2009 | Ellis ....................... | A61K 31/04 514/29 |

FOREIGN PATENT DOCUMENTS

| | | |
|---|---|---|
| EP | 0527101 | 2/1993 |
| TR | 2001 01991 | 2/2003 |
| WO | WO 99/43354 | 9/1999 |

OTHER PUBLICATIONS

Chodosh, S. et al. "Prazosin in hypertensive patients with chronic bronchitis and asthma: A brief report," *American Journal of Medicine*, vol. 86, No. 1, Jan. 23, 1989, pp. 91-93.

(Continued)

*Primary Examiner* — Sreeni Padmanabhan
*Assistant Examiner* — Jody Karol
(74) *Attorney, Agent, or Firm* — Steptoe & Johnson LLP

(57) ABSTRACT

The present invention relates to a combination comprising at least one compound selected from the group consisting of an α-adrenergic antagonist, an anthelmintic agent, an antifungal agent, an antimalarial agent, an antineoplastic agent, an antipsychotic agent, an antioxidant, a vasodilator, a vitamin, or a pharmaceutically acceptable derivative thereof; and an antimicrobial compound.

6 Claims, 15 Drawing Sheets

(56) References Cited

OTHER PUBLICATIONS

Szreder, Z. et al. "Inhibition of pyrogen *Escherichia coli* fever with intracerebral administration of prazosin, dihydrobenzperidol and nifedipin in the rabbits," *General Pharmacology*, vol. 22, No. 2, Jan. 1, 1991, pp. 381-388.

Bermudez et al., "Mefloquine, Moxifloxacin, and Ethanbutol Are a Triple-Drug Alternative to Macrolide-Containing Regimens for Treatment of *Mycobacterium avium* Disease," *Brief Report: J. of Infectious Diseases*, 2003: 187; 1977-1980.

\* cited by examiner

**Bactericidal activity of suloctidil and mefloquine against stationary phase *Pseudomonas aeruginosa***

PHARMACEUTICAL COMPOSITION FOR TREATING A MICROBIAL INFECTION

This invention relates to the use of certain classes of known compounds for the treatment of microbial infections. In particular, it relates to the use of such compounds to kill multiplying, non-multiplying and/or clinically latent microorganisms associated with microbial infections.

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (Nature Reviews, Drug Discovery 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (Lancet 357, 1179 (2001) and Lancet 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (Science 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (J. Antimicrob. Chemother. 4, 395-404 (1988); J. Med. Microbiol. 38, 197-202 (1993); J. Bacteriol. 182, 1794-1801 (2000); ibid. 182, 6358-6365 (2000); ibid. 183, 6746-6751 (2001); FEMS Microbiol. Lett. 202, 59-65 (2001); and Trends in Microbiology 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (Proc. Natl. Acad. Sci. USA 92, 11736-11740 (1995); J. Bacteriol. 179, 6688-6691 (1997); and Antimicrob. Agents Chemother. 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

International Patent Application, Publication Number WO2000028074 describes a method of screening compounds to determine their ability to kill clinically latent microorganisms. Using this method, the Applicant has observed that many conventional antimicrobial agents, such as augmentin, azithromycin, levofloxacin, linezolid and mupirocin, which otherwise exhibit excellent biological activity against log phase (i.e. multiplying) bacteria, exhibit little or no activity against clinically latent microorganisms. This observation has necessitated the development of novel antimicrobials which may be used to kill clinically latent microorganisms.

International Patent Application, Publication Numbers WO2007054693, WO2008117079 and WO2008142384 describe compounds which exhibit biological activity against clinically latent microorganisms. Examples of such compounds include 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, N-[4-(3-benzylpyrrolidin-1-yl)-2-methylquinolin-6-yl]benzamide and pharmaceutically acceptable derivatives thereof.

The present invention is based upon the unexpected finding that certain classes of known biologically active compounds have been found to exhibit bactericidal activity against a variety of microorganisms.

Thus, in one embodiment the present invention provides the use of one or more compounds selected from the following: an α-adrenergic antagonist, an anthelmintic agent, an antifungal agent, an antimalarial agent, an antineoplastic agent, an antipsychotic agent, an antioxidant, a vasodilator and/or a vitamin, or a pharmaceutically acceptable derivative thereof, for the treatment of a microbial infection; with the proviso that when the biologically active agent is an antifungal agent, the microbial infection is a bacterial infection.

In a further embodiment, the invention provides a method of treating a microbial infection which comprises administering to a mammal, including man, one or more compounds selected from the following: an α-adrenergic antagonist, an anthelmintic agent, an antifungal agent, an antimalarial agent, an antineoplastic agent, an antipsychotic agent, an antioxidant, a vasodilator and/or a vitamin, or a pharmaceutically acceptable derivative thereof; with the proviso when the biologically active agent is an antifungal agent, the microbial infection is a bacterial infection.

There is also provided a pharmaceutical composition comprising one or more compounds selected from the following: an α-adrenergic antagonist, an anthelmintic agent, an antifungal agent, an antimalarial agent, an antineoplastic agent, an antipsychotic agent, an antioxidant, a vasodilator and/or a vitamin, or a pharmaceutically acceptable derivative thereof, and a pharmaceutically acceptable adjuvant, diluent or carrier, for use in the treatment of a microbial infection; with the proviso when the biologically active agent is an antifungal agent, the microbial infection is a bacterial infection.

Figure 1:
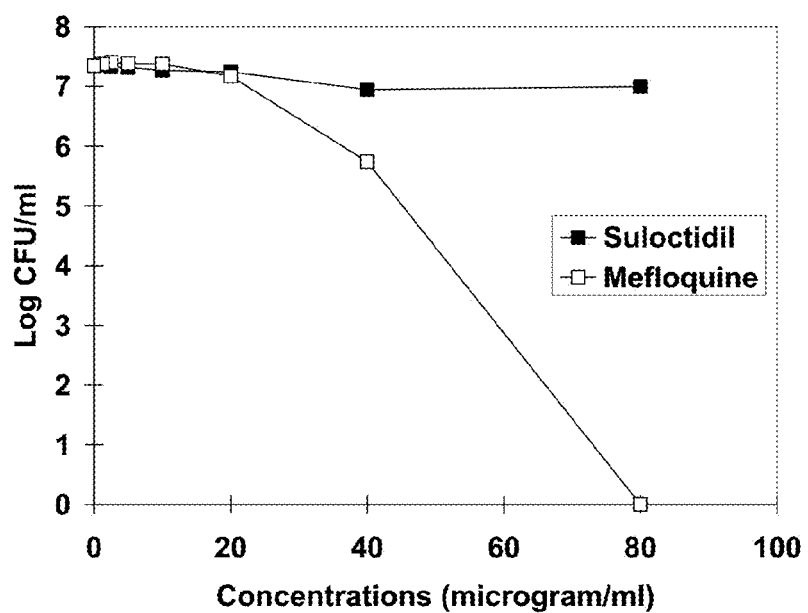
FIG. 1 is a graph showing bacterialcidal activity.
Figure 2:
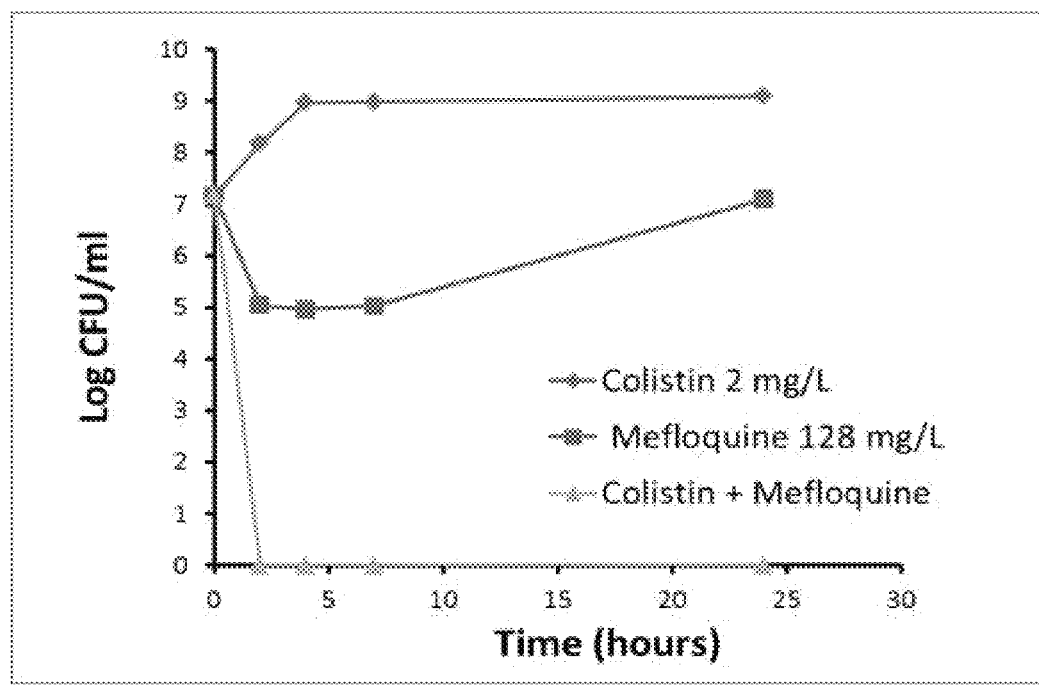
FIGS. 2-15 are graphs depicting time kill curves.
Figure 3:
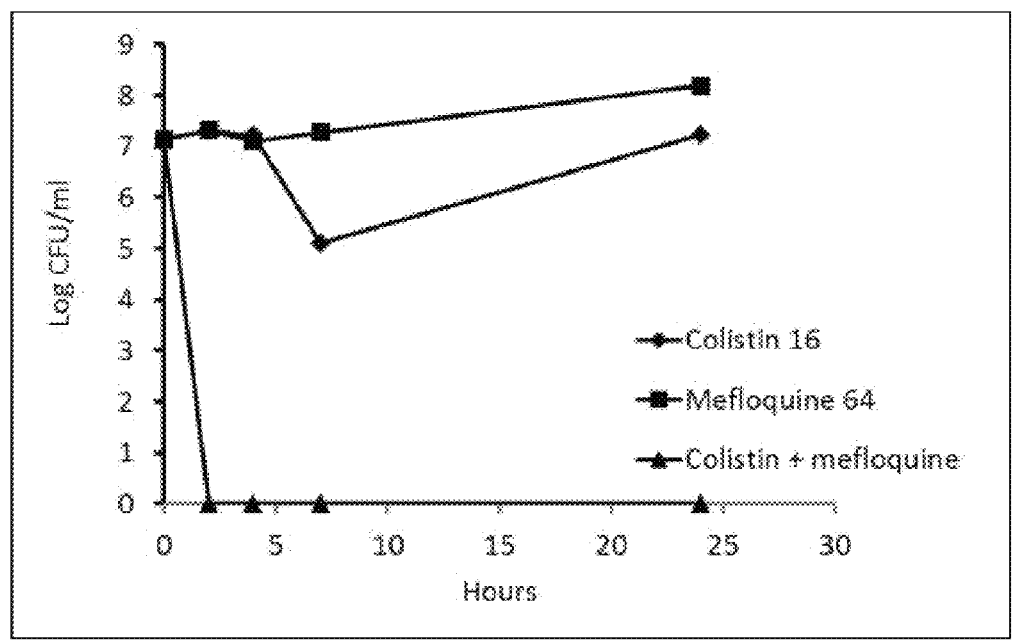
Figure 4:
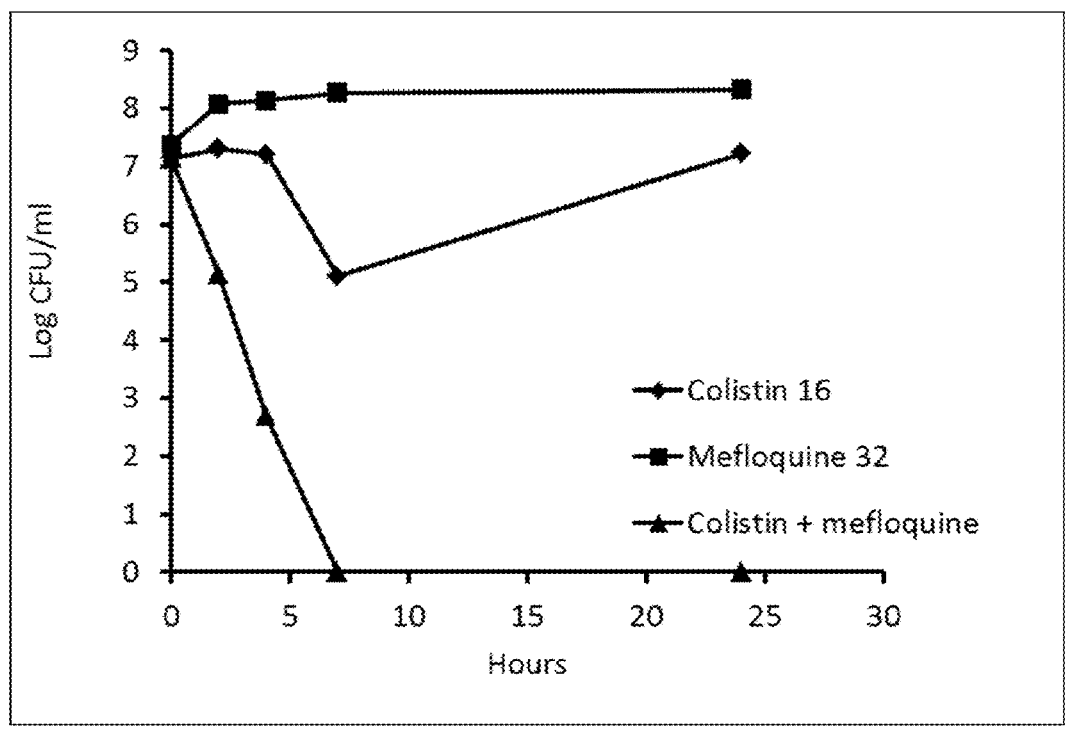
Figure 5:
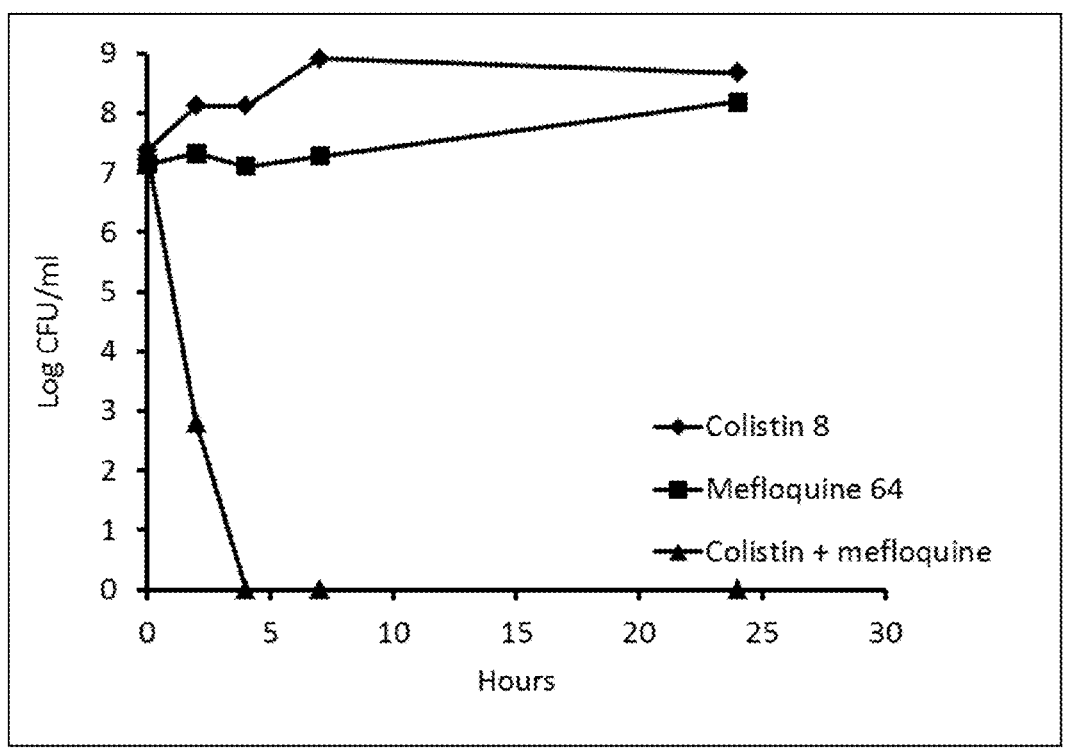
Figure 6:
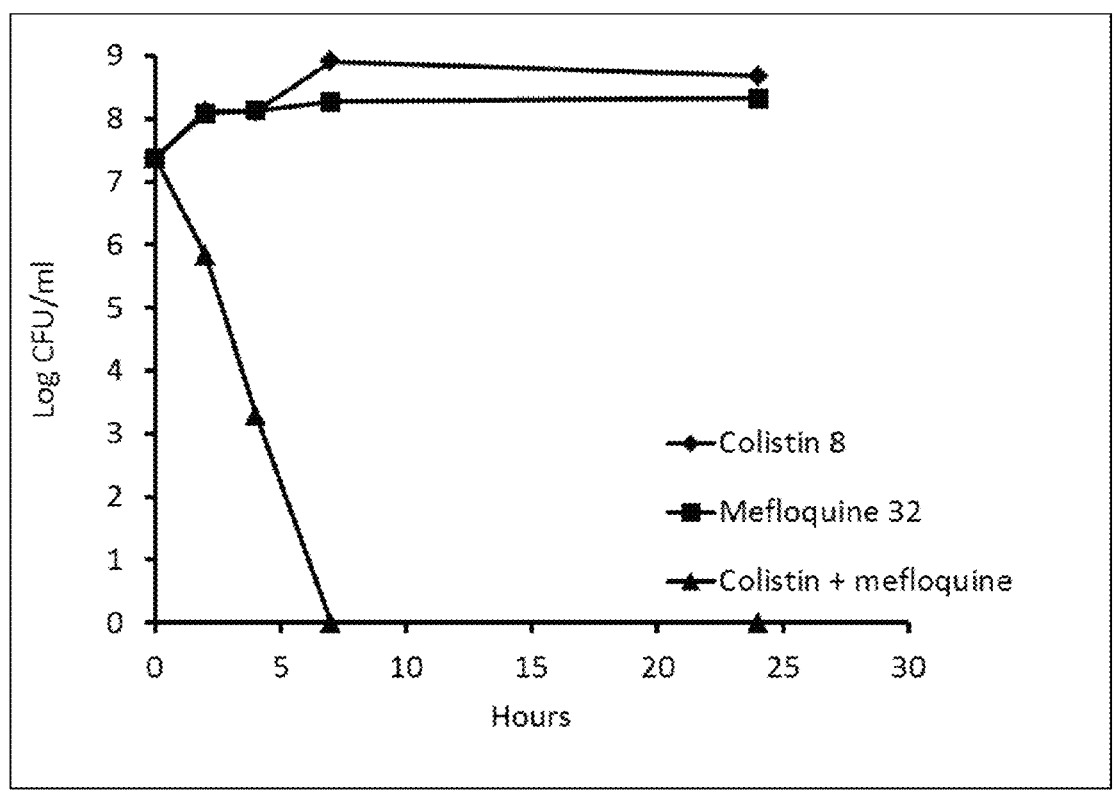
Figure 7:
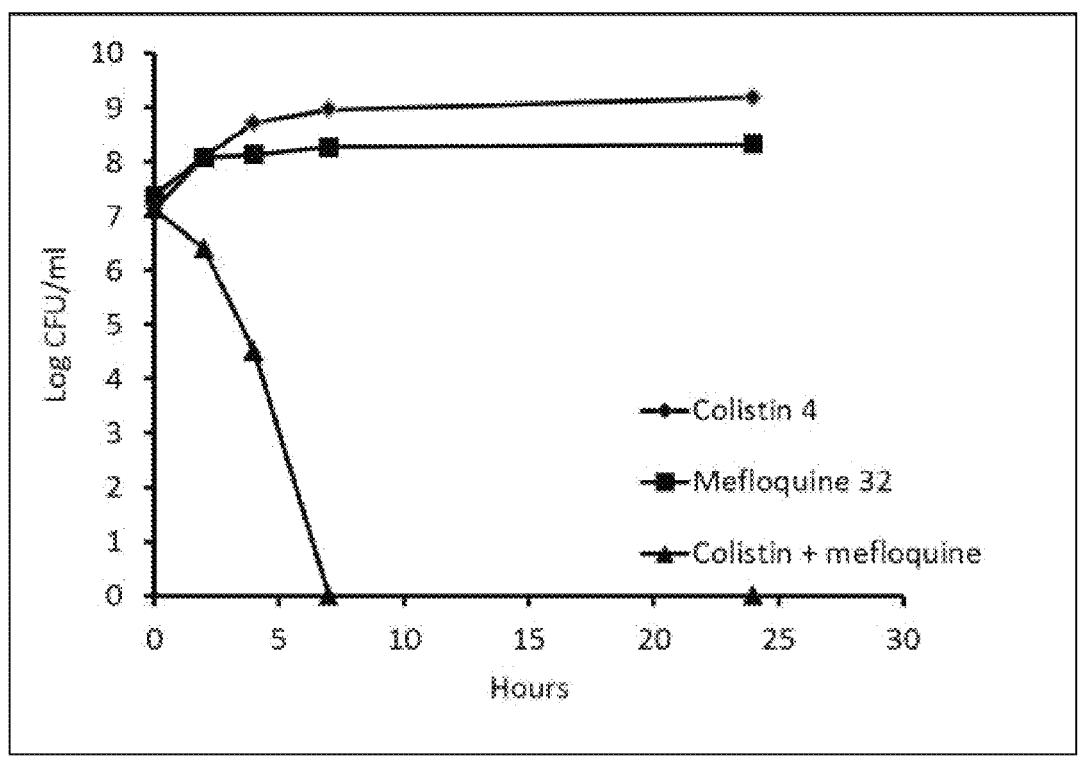
Figure 8:
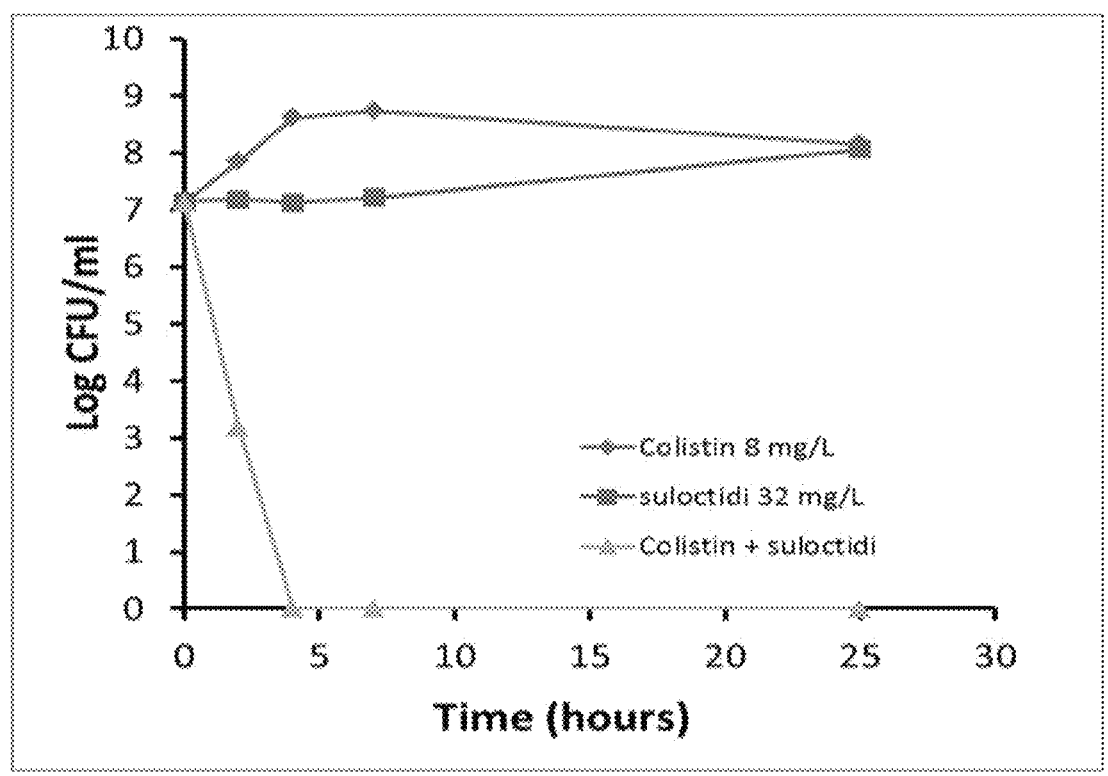
Figure 9:
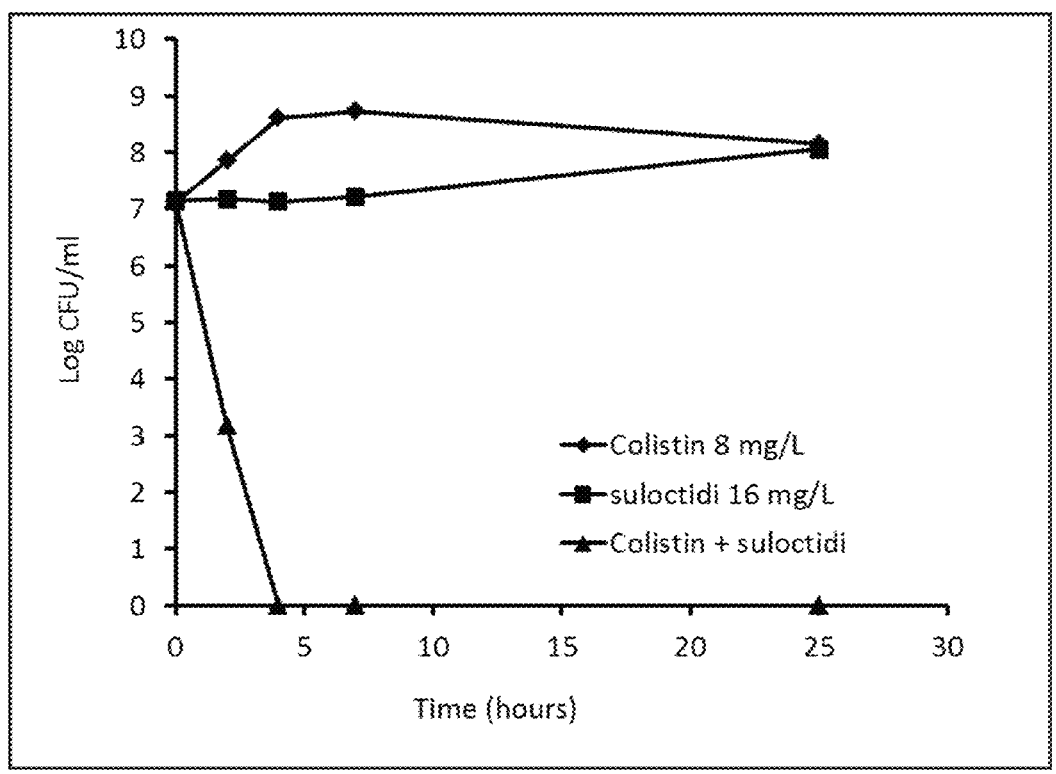
Figure 10:
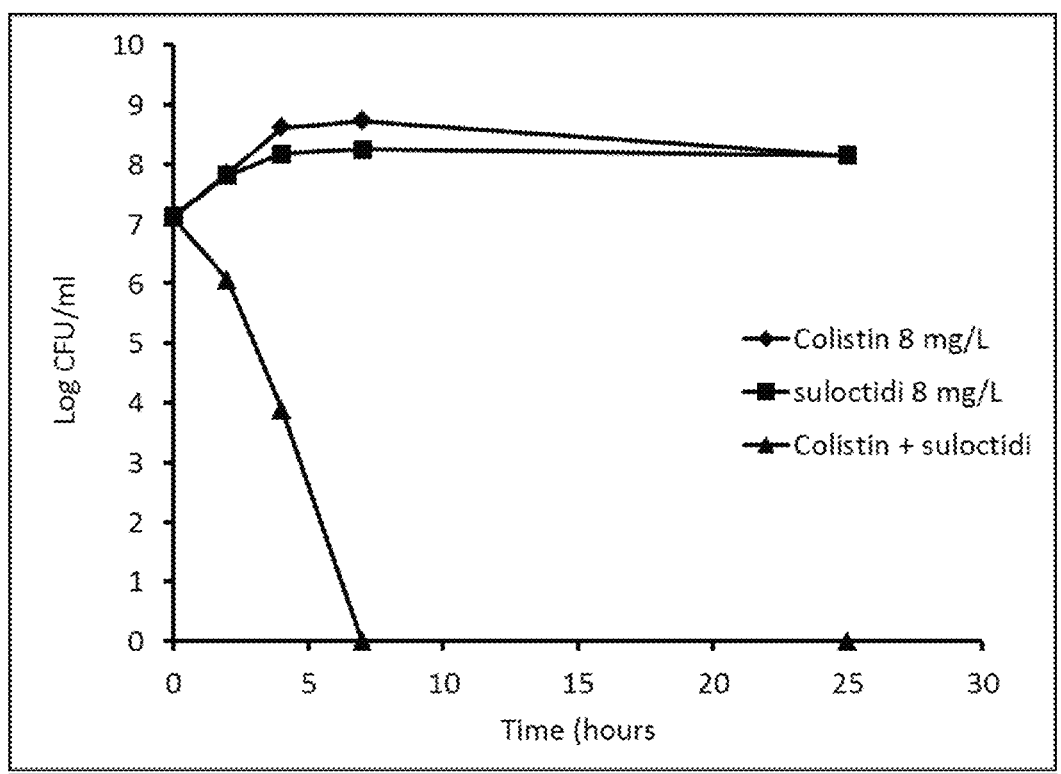
Figure 11:
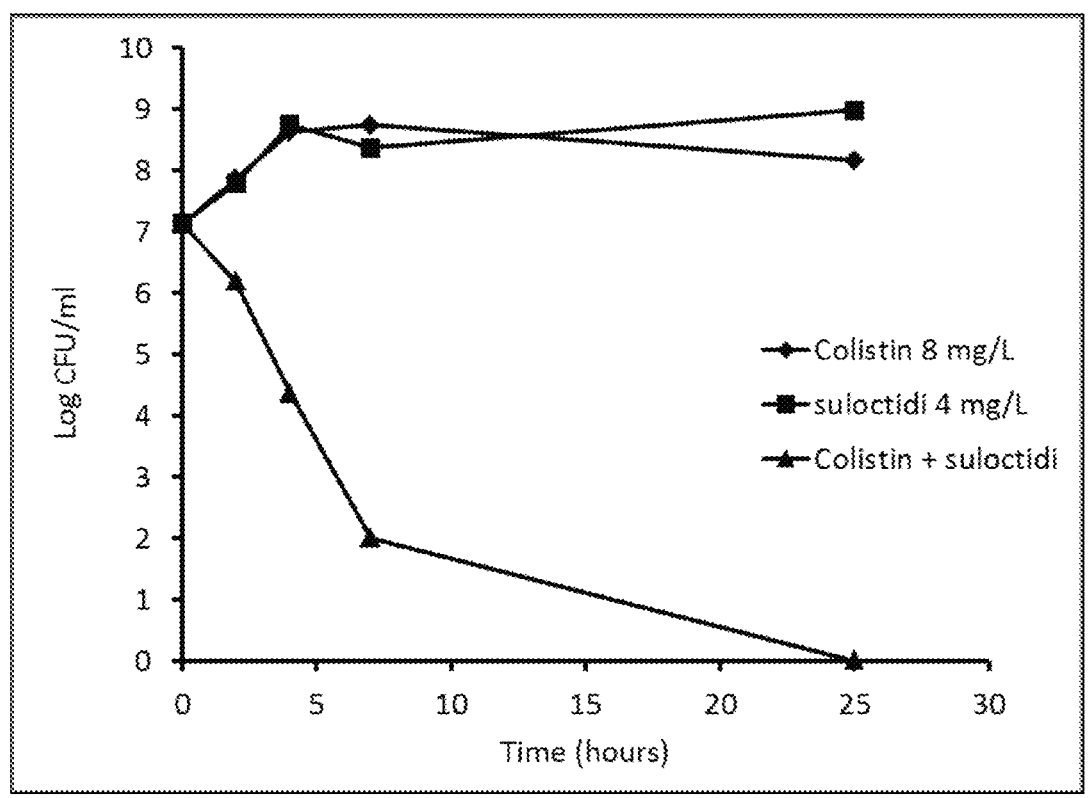

The aforementioned classes of biologically active compounds may be used to treat microbial infections. In particular they may be used to kill multiplying (log phase), non-multiplying (stationary phase) and/or clinically latent (persistent) microorganisms associated with microbial infections. References herein to the treatment of a microbial infection therefore include killing multiplying, non-multiplying and/or clinically latent microorganisms associated with such infections. In a preferred embodiment, the aforementioned compounds are used to kill non-multiplying and/or clinically latent microorganisms, most preferably non-multiplying microorganisms.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:
(I) mRNA (e.g. from 0.0001 to 50%, such as from 1 to 30, 5 to 25 or 10 to 20%, of the level of mRNA); and/or
(II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

In one embodiment of the invention, one or more of the aforementioned classes of biologically active compounds is used to treat a bacterial infection; in particular, the compounds may be used to kill clinically latent microorganisms associated with a bacterial infection. As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pas-*

*teuri*, *Staph. saccharolyticus*, *Staph. schleiferi schleiferi*, *Staph. s. coagulans*, *Staph. sciuri*, *Staph. simulans*, *Staph. warneri* and *Staph. xylosus*);

Streptococci (e.g. beta-haemolytic, pyogenic streptococci (such as *Strept. agalactiae*, *Strept. canis*, *Strept dysgalactiae dysgalactiae*, *Strept. dysgalactiae equisimilis*, *Strept equi equi*, *Strept. equi zooepidemicus*, *Strept. iniae*, *Strept. porcinus* and *Strept. pyogenes*), microaerophilic, pyogenic streptococci (*Streptococcus* "milleri", such as *Strept. anginosus*, *Strept. constellatus constellatus*, *Strept. constellatus pharyngidis* and *Strept. intermedius*), oral streptococci of the "mitis" (alpha-haemolytic-*Streptococcus* "viridans", such as *Strept. mitis*, *Strept. oralis*, *Strept. sanguinis*, *Strept. cristatus*, *Strept. gordonii* and *Strept. parasanguinis*), "salivarius" (non-haemolytic, such as Strept *salivarius* and *Strept. vestibularis*) and "mutans" (tooth-surface streptococci, such as *Strept. criceti*, *Strept. mutans*, *Strept. ratti* and *Strept. sobrinus*) groups, *Strept. acidominimus*, *Strept. bovis*, *Strept. faecalis*, *Strept. equinus*, *Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae*, *Neisseria meningitidis*, *Neisseria cinerea*, *Neisseria elongata*, *Neisseria flavescens*, *Neisseria lactamica*, *Neisseria mucosa*, *Neisseria sicca*, *Neisseria subflava* and *Neisseria weaveri*;

Bacillaceae, such as *Bacillus anthracis*, *Bacillus subtilis*, *Bacillus thuringiensis*, *Bacillus stearothermophilus* and *Bacillus cereus*;

Enterobacteriaceae, such as *Escherichia coli*, *Enterobacter* (e.g. *Enterobacter aerogenes*, *Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii*, *Salmonella* (*Salmonella enterica* and *Salmonella typhi*), *Shigella* (e.g. *Shigella dysenteriae*, *Shigella flexneri*, *Shigella boydii* and *Shigella sonnei*), *Klebsiella* (e.g. *Klebs. pneumoniae*, *Klebs. oxytoca*, *Klebs. ornitholytica*, *Klebs. planticola*, *Klebs. ozaenae*, *Klebs. terrigena*, *Klebs. granulomatis* (*Calymmatobacterium granulomatis*) and *Klebs. rhinoscleromatis*), *Proteus* (e.g. *Pr. mirabilis*, *Pr. rettgeri* and *Pr. vulgaris*), *Providencia* (e.g. *Providencia alcalifaciens*, *Providencia rettgeri* and *Providencia stuartii*), *Serratia* (e.g. *Serratia marcescens* and *Serratia liquifaciens*), and *Yersinia* (e.g. *Yersinia enterocolitica*, *Yersinia pestis* and *Yersinia pseudotuberculosis*);

Enterococci (e.g. *Enterococcus avium*, *Enterococcus casseliflavus*, *Enterococcus cecorum*, *Enterococcus dispar*, *Enterococcus durans*, *Enterococcus faecalis*, *Enterococcus faecium*, *Enterococcus flavescens*, *Enterococcus gallinarum*, *Enterococcus hirae*, *Enterococcus malodoratus*, *Enterococcus mundtii*, *Enterococcus pseudoavium*, *Enterococcus raffinosus* and *Enterococcus solitarius*);

*Helicobacter* (e.g. *Helicobacter pylori*, *Helicobacter cinaedi* and *Helicobacter fennelliae*);

*Acinetobacter* (e.g. *A. baumanii*, *A. calcoaceticus*, *A. haemolyticus*, *A. johnsonii*, *A. junfi*, *A. Iwoffi* and *A. radioresistens*);

*Pseudomonas* (e.g. *Ps. aeruginosa*, *Ps. maltophilia* (*Stenotrophomonas maltophilia*), *Ps. alcaligenes*, *Ps. chlororaphis*, *Ps. fluorescens*, *Ps. luteola*. *Ps. mendocina*, *Ps. monteilii*, *Ps. oryzihabitans*, *Ps. pertocinogena*, *Ps. pseudalcaligenes*, *Ps. putida* and *Ps. stutzeri*);

*Bacteroides fragilis*;

*Peptococcus* (e.g. *Peptococcus niger*);

*Peptostreptococcus*;

*Clostridium* (e.g. *C. perfringens*, *C. difficile*, *C. botulinum*, *C. tetani*, *C. absonum*, *C. argentinense*, *C. baratii*, *C. bifermentans*, *C. beijerinckii*, *C. butyricum*, *C. cadaveris*, *C. camis*, *C. celatum*, *C. clostridioforme*, *C. cochlearium*, *C. cocleatum*, *C. fallax*, *C. ghonii*, *C. glycolicum*, *C. haemolyticum*, *C. hastiforme*, *C. histolyticum*, *C. indolis*, *C. innocuum*, *C. irregulare*, *C. leptum*, *C. limosum*, *C. malenominatum*, *C. novyi*, *C. oroticum*, *C. paraputrificum*, *C. piliforme*, *C. putrefasciens*, *C. ramosum*, *C. septicum*, *C. sordelii*, *C. sphenoides*, *C. sporogenes*, *C. subterminale*, *C. symbiosum* and *C. tedium*);

*Mycoplasma* (e.g. *M. pneumoniae*, *M. hominis*, *M. genitalium* and *M. urealyticum*);

Mycobacteria (e.g. *Mycobacterium tuberculosis*, *Mycobacterium avium*, *Mycobacterium fortuitum*, *Mycobacterium marinum*, *Mycobacterium kansasii*, *Mycobacterium chelonae*, *Mycobacterium abscessus*, *Mycobacterium leprae*, *Mycobacterium smegmitis*, *Mycobacterium africanum*, *Mycobacterium alvei*, *Mycobacterium asiaticum*, *Mycobacterium aurum*, *Mycobacterium bohemicum*, *Mycobacterium bovis*, *Mycobacterium branderi*, *Mycobacterium brumae*, *Mycobacterium celatum*, *Mycobacterium chubense*, *Mycobacterium confluentis*, *Mycobacterium conspicuum*, *Mycobacterium cookii*, *Mycobacterium flavescens*, *Mycobacterium gadium*, *Mycobacterium gastri*, *Mycobacterium genavense*, *Mycobacterium gordonae*, *Mycobacterium goodii*, *Mycobacterium haemophilum*, *Mycobacterium hassicum*, *Mycobacterium intracellulare*, *Mycobacterium interjectum*, *Mycobacterium heidelberense*, *Mycobacterium lentiflavum*, *Mycobacterium malmoense*, *Mycobacterium mucogenicum*, *Mycobacterium microti*, *Mycobacterium mucogenicum*, *Mycobacterium neoaurum*, *Mycobacterium nonchromogenicum*, *Mycobacterium peregrinum*, *Mycobacterium phlei*, *Mycobacterium scrofulaceum*, *Mycobacterium shimoidei*, *Mycobacterium simiae*, *Mycobacterium szulgai*, *Mycobacterium terrae*, *Mycobacterium the rmoresistabile*, *Mycobacterium triplex*, *Mycobacterium triviale*, *Mycobacterium tusciae*, *Mycobacterium ulcerans*, *Mycobacterium vaccae*, *Mycobacterium wolinskyi* and *Mycobacterium xenopi*);

*Haemophilus* (e.g. *Haemophilus influenzae*, *Haemophilus ducreyi*, *Haemophilus aegyptius*, *Haemophilus parainfluenzae*, *Haemophilus haemolyticus* and *Haemophilus parahaemolyticus*);

*Actinobacillus* (e.g. *Actinobacillus actinomycetemcomitans*, *Actinobacillus equuli*, *Actinobacillus hominis*, *Actinobacillus lignieresii*, *Actinobacillus suis* and *Actinobacillus ureae*);

*Actinomyces* (e.g. *Actinomyces israelii*);

*Brucella* (e.g. *Brucella abortus*, *Brucella canis*, *Brucella melintensis* and *Brucella suis*);

*Campylobacter* (e.g. *Campylobacter jejuni*, *Campylobacter coli*, *Campylobacter lari* and *Campylobacter fetus*);

*Listeria monocytogenes*;

*Vibrio* (e.g. *Vibrio cholerae* and *Vibrio parahaemolyticus*, *Vibrio alginolyticus*, *Vibrio carchariae*, *Vibrio fluvialis*, *Vibrio furnissii*, *Vibrio hollisae*, *Vibrio metschnikovii*, *Vibrio mimicus* and *Vibrio vulnificus*);

*Erysipelothrix rhusopathiae*;

Corynebacteriaceae (e.g. *Corynebacterium diphtheriae*, *Corynebacterium jeikeum* and *Corynebacterium urealyticum*);

Spirochaetaceae, such as *Borrelia* (e.g. *Borrelia recurrentis*, *Borrelia burgdorferi*, *Borrelia afzelii*, *Borrelia andersonii*, *Borrelia bissettii*, *Borrelia garinii*, *Borrelia japonica*, *Borrelia lusitaniae*, *Borrelia tanukii*, *Borrelia turdi*, *Borrelia valaisiana*, *Borrelia caucasica*, *Borrelia crocidurae*, *Borre-* lia duttoni, Borrelia graingeri, Borrelia hermsii, Borrelia hispanica, Borrelia latyschewii, Borrelia mazzottii, Borrelia parkeri, Borrelia persica, Borrelia turicatae and Borrelia venezue/ensis) and Treponema (Treponema pallidum ssp. pallidum, Treponema pallidum ssp. endemicum, Treponema pallidum ssp. pertenue and Treponema carateum);

Pasteurella (e.g. Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica and Pasteurella stomatis);

Bordetella (e.g. Bordetella bronchiseptica, Bordetella hinzii, Bordetella holmseii, Bordetella parapertussis, Bordetella pertussis and Bordetella trematum);

Nocardiaceae, such as Nocardia (e.g. Nocardia asteroides and Nocardia brasiliensis);

Rickettsia (e.g. Ricksettsii or Coxiella burnetii);

Legionella (e.g. Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israe/ensis, Legionalla jordanis, Legionalla lansingensis, Legionalla longbeachae, Legionalla maceachernii, Legionalla micdadei, Legionalla oakridgensis, Legionalla pneumophila, Legionalla sainthe/ensi, Legionalla tucsonensis and Legionalla wadsworthii);

Moraxella catarrhalis;
Cyclospora cayetanensis;
Entamoeba histolytica;
Giardia lamblia;
Trichomonas vaginalis;
Toxoplasma gondii;
Stenotrophomonas maltophilia;
Burkholderia cepacia; Burkholderia mallei and Burkholderia pseudomallei;
Francisella tularensis;
Gardnerella (e.g. Gardneralla vaginalis and Gardneralla mobiluncus);
Streptobacillus moniliformis;

Flavobacteriaceae, such as Capnocytophaga (e.g. Capnocytophaga canimorsus, Capnocytophaga cynodegmi, Capnocytophaga gingivalis, Capnocytophaga granulosa, Capnocytophaga haemolytica, Capnocytophaga ochracea and Capnocytophaga sputigena);

Bartonella (Bartonella bacilliformis, Bartonella clarridgeiae, Bartonella elizabethae, Bartonella henselae, Bartonella quintana and Bartonella vinsonii arupensis);

Leptospira (e.g. Leptospira biflexa, Leptospira borgpetersenii, Leptospira inadai, Leptospira interrogans, Leptospira kirschneri, Leptospira noguchii, Leptospira santarosai and Leptospira weilii);

Spirillium (e.g. Spirillum minus);

Baceteroides (e.g. Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus and Bacteroides vulgatus);

Prevotella (e.g. Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis and Prevotella zoogleoformans);

Porphyromonas (e.g. Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levil and Porphyromonas macacae);

Fusobacterium (e.g. F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans and F. varium);

Chlamydia (e.g. Chlamydia trachomatis);

Cryptosporidium (e.g. C. parvum, C. hominis, C. canis, C. felis, C. meleagridis and C. muris);

Chlamydophila (e.g. Chlamydophila abortus (Chlamydia psittaci), Chlamydophila pneumoniae (Chlamydia pneumoniae) and Chlamydophila psittaci (Chlamydia psittaci));

Leuconostoc (e.g. Leuconostoc citreum, Leuconostoc cremoris, Leuconostoc dextranicum, Leuconostoc lactis, Leuconostoc mesenteroides and Leuconostoc pseudomesenteroides);

Gemella (e.g. Gemella bergeri, Gemella haemolysans, Gemella morbillorum and Gemella sanguinis); and Ureaplasma (e.g. Ureaplasma parvum and Ureaplasma urealyticum).

Preferably the bacteria to be treated are selected from the group consisting of:

Staphylococci, such as Staph. aureus (either Methicillin-sensitive (i.e. MSSA) or Methicillin-resistant (i.e. MRSA)) and Staph. epidermidis;

Streptococci, such as Strept. agalactiae and Strept. pyogenes;

Bacillaceae, such as Bacillus anthracis;

Enterobacteriaceae, such as Escherichia coli, Klebsiella (e.g. Klebs. pneumoniae and Klebs. oxytoca) and Proteus (e.g. Pr. mirabilis, Pr. rettgeri and Pr. vulgaris); Haemophilis influenzae;

Enterococci, such as Enterococcus faecalis and Enterococcus faecium; and

Mycobacteria, such as Mycobacterium tuberculosis.

More preferably, the bacteria to be treated are selected from the group consisting of Staphylococcus aureus; either MSSA or MRSA, Escherichia coli and Pseudomonas aeruginosa.

In another embodiment of the invention, one or more of the aforementioned classes of biologically active compounds, excluding antifungal agents, is used to treat a fungal infection; in particular, the compounds may be used to kill clinically latent microorganisms associated with a fungal infection. As used herein, the term "fungi" (and derivatives thereof, such as "fungal infection") includes, but is not limited to, references to organisms (or infections due to organisms) of the following classes and specific types:

Absidia (e.g. Absidia corymbifera);

Ajellomyces (e.g. Ajellomyces capsulatus and Ajellomyces dermatitidis);

Arthroderma (e.g. Arthroderma benhamiae, Arthroderma fulvum, Arthroderma gypseum, Arthroderma incurvatum, Arthroderma otae and Arthroderma vanbreuseghemii);

Aspergillus (e.g. Aspergillus flavus, Aspergillus fumigatus and Aspergillus niger);

Blastomyces (e.g. Blastomyces dermatitidis);

*Candida* (e.g. *Candida albicans, Candida glabrata, Candida guilliermondii, Candida krusei, Candida parapsilosis, Candida tropicalis* and *Candida pelliculosa*);

*Cladophialophora* (e.g. *Cladophialophora carrionii*);

*Coccidioides* (e.g. *Coccidioides immitis* and *Coccidioides posadasii*);

*Cryptococcus* (e.g. *Cryptococcus neoformans*);

*Cunninghamella* (e.g. *Cunninghamella* sp.)

*Epidermophyton* (e.g. *Epidermophyton floccosum*);

*Exophiala* (e.g. *Exophiala dermatitidis*);

*Filobasidiella* (e.g. *Filobasidiella neoformans*);

*Fonsecaea* (e.g. *Fonsecaea pedrosoi*);

*Fusarium* (e.g. *Fusarium solani*);

*Geotrichum* (e.g. *Geotrichum candidum*);

*Histoplasma* (e.g. *Histoplasma capsulatum*);

*Hortaea* (e.g. *Hortaea werneckii*);

*Issatschenkia* (e.g. *Issatschenkia orientalis*);

*Madurella* (e.g. *Madurella grisae*);

*Malassezia* (e.g. *Malassezia furfur, Malassezia globosa, Malassezia obtusa, Malassezia pachydermatis, Malassezia restricta, Malassezia slooffiae* and *Malassezia sympodialis*);

*Microsporum* (e.g. *Microsporum canis, Microsporum fulvum* and *Microsporum gypseum*);

*Microsporidia;*

*Mucor* (e.g. *Mucor circinelloides*);

*Nectria* (e.g. *Nectria haematococca*);

*Paecilomyces* (e.g. *Paecilomyces variotii*);

*Paracoccidioides* (e.g. *Paracoccidioides brasiliensis*);

*Penicillium* (e.g. *Penicillium marneffei*);

*Pichia* (e.g. *Pichia anomala* and *Pichia guilliermondii*);

*Pneumocystis* (e.g. *Pneumocystis jiroveci* (*Pneumocystis carinii*));

*Pseudallescheria* (e.g. *Pseudallescheria boydii*);

*Rhizopus* (e.g. *Rhizopus oryzae*);

*Rhodotorula* (e.g. *Rhodotorula rubra*);

*Scedosporium* (e.g. *Scedosporium apiospermum*);

*Schizophyllum* (e.g. *Schizophyllum commune*);

*Sporothrix* (e.g. *Sporothrix schenckii*);

*Trichophyton* (e.g. *Trichophyton mentagrophytes, Trichophyton rubrum, Trichophyton verrucosum* and *Trichophyton violaceum*); and

*Trichosporon* (e.g. *Trichosporon asahii, Trichosporon cutaneum, Trichosporon inkin* and *Trichosporon mucoides*).

Preferably, the fungi to be treated are selected from the group consisting of *Aspergillus fumigatus, Candida albicans, Cryptococcus neoformans, Histoplasma capsulatum* and *Pneumocystis jiroveci.*

The biologically active compounds for use in the present invention are commercially available and/or may be prepared using conventional methods known in the art.

Examples of suitable α-adrenergic antagonists (α-blockers) include non-selective α-adrenergic antagonists, $α_1$-adrenergic antagonists and/or $α_2$-adrenergic antagonists. Preferred examples of α-adrenergic antagonists include one or more compounds selected from the group consisting of: phenoxybenzamine, phentolamine, tolazoline, alfuzosin, prazosin, doxazosin, tamsulosin, terazosin, atipamezole, idazoxan and/or yohimbine, and pharmaceutically acceptable derivatives thereof. Most preferably, the α-adrenergic antagonist is phenoxybenzamine or a pharmaceutically acceptable derivative thereof, such as phenoxybenzamine hydrochloride.

An anthelmintic agent is a compound used to treat infections with parasitic worms, including flat worms, such as flukes and tapeworms, and round worms, such as nematodes. Examples of suitable anthelmintic agents include one or more compounds selected from the group consisting of: abamectin, albendazole, bithionate (such as bithionate sodium), closantel, diethylcarbamazine, emodepside, fenbendazole, flubendazole, ivermectin, levamisole, mebendazole, metrifonate, morantel, monepantel, niclosamide, oxamnaquine, pararosaniline (such as pararosaniline pamoate), piperazine (such as piperazine citrate and piperazine hydrate), praziquantel, pyrvinium (such as pyrvinium pamoate), pyrantel (such as pyrantel pamoate), quinacrine (such as quinacrine hydrochloride), suramin, thiabendazole and/or triclabendazole, and pharmaceutically acceptable derives thereof. Preferably, the anthelmintic agent is selected from one or more of the following compounds: bithionate sodium, pararosaniline pamoate, pyrvinium pamoate, and/or quinacrine hydrochloride.

An antifungal agent is a compound used to treat fungal infections. Examples of suitable antifungal agents include one or more compounds selected from the group consisting of: abafungin, acrisorcin, anidulafungin, amorolfine, amphotericin B, butenafine, candicin, caspofungin, filipin, hamycin, natamycin, nystatin, rimocidin, bifonazole, butoconazole, clotrimazole, econazole, fenticonazole, fluconazole, isoconazole, itraconazole, isavuconazole, ketoconazole, naftifine, micafungin miconazole, oxiconazole, phenylmercuric acetate, posaconazole, ravuconazole, sertraconazole, sulconazole, terbinafine, terconazole, tioconazole and/or voriconazole, and pharmaceutically acceptable derives thereof. Preferably, the antifungal agent is selected from one or more of the following compounds: acrisorcin, phenylmercuric acetate and/or tioconazole.

An antimalarial agent is a compound used to prevent and/or treat malaria. Examples of suitable antimalarial agents include one or more compounds selected from the group consisting of: amodiaquine, atovaquone, chloroquine, cinchoine, cinchonidine, doxycycline, halofantrine, primaquine, proguanil, pyrimethamine, mefloquine, quinine, quinidine, sulfadoxine and/or sulfamethoxypyridazine, and pharmaceutically acceptable derivatives thereof. Preferably, the antimalarial agent is mefloquine.

An antineoplastic agent is a compound used to treat cancer. Examples of suitable antineoplastic agents include one or more compounds selected from the group consisting of: actinomycin, afimoxifene, arzoxifene, bazedoxifene, bleomycin, carboplatin, cisplatin, cyclofenil, daunorubicin, doxorubicin, epirubicin, idarubicin, lasofoxifene, mitomycin C, mitoxanthrone (such as mitoxanthrone hydrochloride), ormeloxifene, plicamycin, raloxifene, sanguinarine sulphate, tamoxifen, toremifene (such as toremifene citrate), and/or valrubicin, and pharmaceutically acceptable derivatives thereof. Preferably, the antineoplastic agent is selected from one or more of the following compounds: bleomycin, carboplatin, cisplatin, doxorubicin, mitomycin C, mitoxanthrone hydrochloride, sanguinarine sulphate and/or toremifene citrate.

An antipsychotic agent is a compound used to manage psychosis, particularly associated with schizophrenia and bipolar disorder. Examples of suitable antipsychotic agents include one or more compounds selected from the group consisting of: chlorpromazine, chlorprothixene (such as chlorprothixene hydrochloride), clopenthixol, flupenthixol, fluphenazine, levomepromazine, mesoridazine, periciazine, perphenazine, pimozide, prochlorperazine, promethazine, promazine, thioridazine (such as thioridazine hydrochloride), thiothixene, trifluoperazine (such as trifluoperazine hydrochloride), triflupromazine (such as triflupromazine hydrochloride), zuclopenthixol, and pharmaceutically acceptable derivatives thereof. Preferably, the antipsychotic agent agent is selected from one or more of the following compounds: chlorprothixene hydrochloride, thioridazine hydrochloride, trifluoperazine hydrochloride and/or triflupromazine hydrochloride.

An antioxidant is a compound that may protect cells against the effects of free radicals. Examples of suitable antioxidants include one or more compounds selected from the group consisting of: carotenoids such as beta-carotene, co-enzyme Q10, hydroquinone, lutein, lycopene, selenium, vitamin A, vitamin C and/or vitamin E, and pharmaceutically acceptable derivatives thereof.

A vasodilator is a compound that relaxes the smooth muscle in blood vessels, which causes the vessels to dilate. Examples of suitable vasodilators include one or more compounds selected from the group consisting of: amlodipine, arandipine, azapetine, azelnidipine, barnidipine, bencyclane, benidipine, bepridil, buflomedil, butalamine, cetiedil, cilnidipine, cinepazide, clentiazem, clevidipine, cyclandelate, diltiazem, efonidipine, fasudil, felodipine, fendiline, gallopamil, ifenprodil, isradipine, lacidipine, lidoflazine, lercanidipine, manidipine, moxisylyte, naftidrofuryl, nicardipine, nifedipine, nilvadipine, nimodipine, nisoldipine, nitrendipine, perhexiline (such as perhexiline maleate), phenoxybenzamine, pranidipine, verapamil, vinburnine, vincamine and/or visnadine, and pharmaceutically acceptable derivatives thereof. Preferably, the vasodilator is selected from one or more of the following compounds: perhexiline maleate, suloctidil and/or nisoldipine.

A vitamin is an organic compound required as a nutrient by an organism. Examples of suitable vitamins include one or more compounds selected from the group consisting of: vitamin A, vitamin B1, vitamin B2, vitamin B3, vitamin B5, vitamin B6, vitamin B7, vitamin B9, vitamin B12, vitamin C, vitamin D, vitamin E and/or vitamin K, and pharmaceutically acceptable derivatives thereof. Preferrably, the vitamin is vitamin B12.

In one embodiment of the invention, there is provided the use of a compound selected from the group consisting of phenoxybenzamine hydrochloride, pyrvinium pamoate, pararosaniline pamoate, bithionate sodium, phenylmercuric acetate, tioconazole, mefloquine, mitomycin C, toremifene citrate, sanguinarine sulphate, carboplatin, cisplatin, hydroquinone, thioridazine hydrochloride, trifluoperazine hydrochloride, triflupromazine hydrochloride, chlorprothixene hydrochloride, perhexiline maleate, suloctidil, nisoldipine, quinacrine hydrochloride, acrisorcin, mitoxanthrone hydrochloride, bleomycin, doxorubicin and vitamin B12 for the treatment of a microbial infection; preferably for killing multiplying, non-multiplying and/or clinically latent microorganisms associated with a microbial infection.

In an alternative embodiment of the invention, there is provided the use of a compound selected from the group consisting of pyrvinium pamoate, pararosaniline pamoate, bithionate sodium, phenylmercuric acetate, tioconazole, mefloquine, mitomycin C, toremifene citrate, sanguinarine sulphate, carboplatin, cisplatin, hydroquinone, thioridazine hydrochloride, trifluoperazine hydrochloride, triflupromazine hydrochloride, chlorprothixene hydrochloride, perhexiline maleate, suloctidil and nisoldipine for the treatment of a microbial infection; preferably a bacterial infection; more preferably an infection caused by S. Aureus, including MSSA and/or MRSA; in particular for killing stationary phase S. Aureus.

In another embodiment of the invention, there is provided the use of a compound selected from the group consisting of quinacrine hydrochloride, pararosaniline pamoate, phenylmercuric acetate, acrisorcin, mefloquine, mitomycin C, mitoxanthrone hydrochloride, bleomycin, doxorubicin, sanguinarine sulfate, carboplatin, cisplatin, hydroquinone, thioridazine hydrochloride, trifluoperazine hydrochloride, triflupromazine hydrochloride, chlorprothixene hydrochloride, perhexiline maleate, suloctidil and vitamin B12 for the treatment of a microbial infection; preferably a bacterial infection; more preferably an infection caused by *Escherichia coli*; in particular, for killing log phase and/or stationary phase *E. coli*.

In a further embodiment of the invention there is provided the use mefloquine for the treatment of a bacterial infection caused by *Pseudomonas aeruginosa*; in particular, for killing stationary phase *Pseudomonas aeruginosa*.

The above-mentioned classes of biologically active compounds have surprisingly been found to possess bactericidal activity and may therefore be used to treat a wide variety of conditions. Particular conditions which may be treated using such classes of compounds according to the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, *pityriasis versicolor*, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis* and *Enterococcus faecium*.

It will be appreciated that references herein to "treatment" extend to prophylaxis as well as the treatment of established diseases or symptoms.

The above-mentioned classes of known biologically active compounds may be used alone or in combination for the treatment of microbial infections. They may also be used in combination with known antimicrobial compounds.

In one embodiment of the invention there is provided a combination comprising at least one compound selected from the group consisting of an α-adrenergic antagonist, an anthelmintic agent, an antifungal agent, an antimalarial agent, an antineoplastic agent, an antipsychotic agent, an antioxidant, a vasodilator, a vitamin, or a pharmaceutically acceptable derivative thereof, and an antimicrobial compound. Preferably said combination is used for killing multiplying, non-multiplying and/or clinically latent microorganisms associated with a microbial infection.

Suitable antimicrobial compounds for use in combination in accordance with the present invention include one or more compounds selected from the following:

(1) β-Lactams, including:
  (i) penicillins, such as
    (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(-)-penicillamine, dicloxacillin, nafcillin and oxacillin,
    (II) penicillinase-resistant penicillins (e.g. flucloxacillin),
    (III) broad-spectrum penicillins (e.g. ampicillin, amoxicillin, metampicillin and bacampicillin),
    (IV) antipseudomonal penicillins (e.g. carboxypenicillins such as ticarcillin or ureidopenicillins such as piperacillin),
    (V) mecillinams (e.g. pivmecillinam), or
    (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and
  (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and R04908463 (CS-023)), penems (e.g. faropenem) and 1-oxa-β-lactams (e.g. moxalactam).

(2) Tetracyclines, such as tetracycline, demeclocycline, doxycycline, lymecycline, minocycline, oxytetracycline, chlortetracycline, meclocycline and methacycline, as well as glycylcyclines (e.g. tigecycline).

(3) Aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.

(4) (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.
  (ii) Ketolides such as telithromycin and cethromycin (ABT-773).
  (iii) Lincosamines, such as lincomycin.

(5) Clindamycin and clindamycin 2-phosphate.

(6) Phenicols, such as chloramphenicol and thiamphenicol.

(7) Steroids, such as fusidic acid (optionally in metal salt form, e.g. in salt form with an alkali metal such as sodium).

(8) Glycopeptides such as vancomycin, teicoplanin, bleomycin, phleomycin, ristomycin, telavancin, dalbavancin and oritavancin.

(9) Oxazolidinones, such as linezolid and AZD2563.

(10) Streptogramins, such as quinupristin and dalfopristin, or a combination thereof.

(11) (i) Peptides, such as polymyxins (e.g. polymyxin E (colistin) and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.
  (ii) Lipopeptides, such as daptomycin.
  (iii) Lipoglycopeptides, such as ramoplanin.

(12) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.

(13) Trimethoprim, optionally in combination with a sulfonamide, such as sulfamethoxazole (e.g. the combination co-trimoxazole).

(14) Antituberculous drugs, such as isoniazid, rifampicin, rifabutin, pyrazinamide, ethambutol, streptomycin, amikacin, capreomycin, kanamycin, quinolones (e.g. those at (q) below), para-aminosalicylic acid, cycloserine and ethionamide.

(15) Antileprotic drugs, such as dapsone, rifampicin and clofazimine.

(16) (i) Nitroimidazoles, such as metronidazole and tinidazole.
  (ii) Nitrofurans, such as nitrofurantoin.

(17) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S-(-)-nadifloxacin), 8-quinolinol, cinoxacin, enrofloxacin, flumequine, lomefloxacin, oxolinic acid and pipemidic acid.

(18) Amino acid derivatives, such as azaserine, bestatin, D-cycloserine, 1,10-phenanthroline, 6-diazo-5-oxo-L-norleucine and L-alanyl-L-1-aminoethyl-phosphonic acid.

(19) Aureolic acids, such as chromomycin A3, mithramycin A and mitomycin C C.
(20) Benzochinoides, such as herbimycin A.
(21) Coumarin-glycosides, such as novobiocin.
(22) Diphenyl ether derivatives, such as irgasan.
(23) Epipolythiodixopiperazines, such as gliotoxin from *Gliocladium fimbriatum*.
(24) Fatty acid derivatives, such as cerulenin.
(25) Glucosamines, such as 1-deoxymannojirimycin, 1-deoxynojirimycin and N-methyl-1-deoxynojirimycin.
(26) Indole derivatives, such as staurosporine.
(27) Diaminopyrimidines, such as iclaprim (AR-100).
(28) Macrolactams, such as ascomycin.
(29) Taxoids, such as paclitaxel.
(30) Statins, such as mevastatin.
(31) Polyphenolic acids, such as (+)-usnic acid.
(32) Polyethers, such as lasalocid A, Ionomycin A, monensin, nigericin and salinomycin.
(33) Picolinic acid derivatives, such as fusaric acid.
(34) Peptidyl nucleosides, such as blasticidine S, nikkomycin, nourseothricin and puromycin.
(35) Nucleosides, such as adenine 9-β-D-arabinofuranoside, 5-azacytidine, cordycepin, formycin A, tubercidin and tunicamycin.
(36) Pleuromutilins, such as GSK-565154, GSK-275833 and tiamulin.
(37) Peptide deformylase inhibitors, such as LBM415 (NVP PDF-713) and BB 83698.
(38) Antibacterial agents for the skin, such as fucidin, benzamycin, clindamycin, erythromycin, tetracycline, silver sulfadiazine, chlortetracycline, metronidazole, mupirocin, framycitin, gramicidin, neomycin sulfate, polymyxins (e.g. polymixin B) and gentamycin.
(39) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.
(40) Antiseptic agents, such as chlorhexidine, phenol derivatives (e.g. thymol and triclosan), quarternary ammonium compounds (e.g. benzalkonium chloride, cetylpyridinium chloride, benzethonium chloride, cetrimonium bromide, cetrimonium chloride and cetrimonium stearate), octenidine dihydrochloride, and terpenes (e.g. terpinen-4-ol).

A preferred combination of the present invention comprises polymyxin E (colistin) and phenoxybenzamine or a pharmaceutically acceptable derivative thereof, such as phenoxybenzamine hydrochloride.

Preferred antimicrobial compounds for use in combination in accordance with the present invention are those capable of killing clinically latent microorganisms. Methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound. A suitable compound screening method against clinically latent microorganisms is described in WO2000028074, the contents of which are incorporated herein by reference as if the publication was specifically and fully set forth herein.

Examples of compounds capable of killing clinically latent microorganisms include those compounds disclosed in International Patent Application, Publication Numbers WO2007054693, WO2008117079 and WO2008142384. These applications describe suitable methods for the preparation of such compounds and doses for their administration.

Preferred examples of antimicrobial agents for use in combination in accordance with the present invention include a compound selected from the group consisting of:
6,8-dimethoxy-4-methyl-1-(3-phenoxyphenyl)-2,3-dihydro-1H-pyrrolo[3,2-c]-quinoline;
6,8-dimethoxy-4-methyl-1-(2-phenoxyethyl)-2,3-dihydro-1H-pyrrolo[3,2-c]-quinoline;
1-cyclopropyl-6,8-dimethoxy-4-methyl-2,3-dihydro-1H-pyrrolo[3,2-c]-quinoline;
8-methoxy-4-methyl-1-(4-phenoxyphenyl)-2,3-dihydro-1H-pyrrolo[3,2-c]-quinoline;
{2-[4-(8-methoxy-4-methyl-2,3-dihydro-1H-pyrrolo[3,2-c]quinolin-1-yl)-phenoxy]ethyl}dimethylamine;
8-methoxy-4-methyl-1-[4-(pyridin-3-yloxy)phenyl]-2,3-dihydro-1H-pyrrolo[3,2-c]quinoline;
4-methyl-8-phenoxy-1-phenyl-2,3-dihydro-1H-pyrrolo[3,2-c]quinoline;
1-benzyl-4-methyl-8-phenoxy-2,3-dihydro-1H-pyrrolo[3,2-c]quinoline
1-(indan-2-yl)-4-methyl-8-phenoxy-2,3-dihydro-1H-pyrrolo[3,2-c]quinoline
4-methyl-6-phenoxy-1-phenyl-2,3-dihydro-1H-pyrrolo[3,2-c]quinoline;
1-benzyl-4-methyl-6-phenoxy-2,3-dihydro-1H-pyrrolo[3,2-c]quinoline;
1-(indan-2-yl)-4-methyl-6-phenoxy-2,3-dihydro-1H-pyrrolo[3,2-c]quinoline;
4-methyl-1-(2-phenylethyl)-8-phenoxy-2,3-dihydro-1H-pyrrolo[3,2-c]-quinoline;
8-methoxy-4-methyl-1-(2-phenylethyl)-2,3-dihydro-1H-pyrrolo[3,2-c]-quinolin-6-ol;
1-(1-benzyl-piperidin-4-yl)-4-methyl-8-phenoxy-2,3-dihydro-1H-pyrrolo[3,2-c]quinoline;
1-(indan-1-yl)-4-methyl-8-phenoxy-2,3-dihydro-1H-pyrrolo[3,2-c]quinoline;
1-(benzodioxan-2-ylmethyl)-4-methyl-8-phenoxy-2,3-dihydro-1H-pyrrolo[3,2-c]quinoline;
4-methyl-8-phenoxy-1-(1,2,3,4-tetrahydronaphthalen-1-yl)-2,3-dihydro-1H-pyrrolo[3,2-c]quinoline;
1-cyclohexyl-4-methyl-8-phenoxy-2,3-dihydro-1H-pyrrolo[3,2-c]quinoline;
8-ethoxy-4-methyl-1-(4-phenoxyphenyl)-2,3-dihydro-1H-pyrrolo[3,2-c]-quinoline;
1-(4-methoxyphenyl)-4-methyl-8-phenoxy-2,3-dihydro-1H-pyrrolo[3,2-c]-quinoline;
4-methyl-1-(4-phenoxyphenyl)-2,3-dihydro-1H-pyrrolo[3,2-c]-quinoline;
4-methyl-1-(2-methylphenyl)methyl-8-phenoxy-2,3-dihydro-1H-pyrrolo[3,2-c]quinoline;
4-methyl-8-phenoxy-1-(4-iso-propylphenyl)-2,3-dihydro-1H-pyrrolo[3,2-c]-quinoline;
4-methyl-8-phenoxy-1-(1-phenylethyl)-2,3-dihydro-1H-pyrrolo[3,2-c]-quinoline;
8-methoxy-4-methyl-1-(2-phenylethyl)-2,3-dihydro-1H-pyrrolo[3,2-c]-quinoline;
6,8-dimethoxy-1-(4-hydroxyphenyl)-4-methyl-2,3-dihydro-1H-pyrrolo[3,2-c]-quinoline;
6,8-dimethoxy-1-(3-hydroxyphenyl)-4-methyl-2,3-dihydro-1H-pyrrolo[3,2-c]-quinoline;
6,8-dimethoxy-1-(3-hydroxy-5-methylphenyl)-4-methyl-2,3-dihydro-1H-pyrrolo[3,2-c]-quinoline;
8-methoxy-1-(4-methoxyphenyl)-4-methyl-2,3-dihydro-1H-pyrrolo[3,2-c]-quinoline;
8-trifluoromethoxy-1-(4-phenoxyphenyl)-4-methyl-2,3-dihydro-1H-pyrrolo[3,2-c]quinoline;

6,8-dimethoxy-4-methyl-1-[4-(pyridin-3-yloxy)phenyl]-2,3-dihydro-1H-pyrrolo[3,2-c]quinoline;
1-benzyl-6,8-dimethoxy-4-methyl-2,3-dihydro-1H-pyrrolo[3,2-c]quinoline;
6,8-dimethoxy-4-methyl-1-(2-phenylethyl)-2,3-dihydro-1H-pyrrolo[3,2-c]quinoline;
4-methyl-1-(2-phenylethyl)-8-trifluoromethoxy-2,3-dihydro-1H-pyrrolo[3,2-c]quinoline;
6,8-dimethoxy-1-(indan-1-yl)-4-methyl-2,3-dihydro-1H-pyrrolo[3,2-c]-quinoline;
6,8-dimethoxy-4-methyl-1-[(6-phenoxy)pyridin-3-yl]-2,3-dihydro-1H-pyrrolo[3,2-c]quinoline;
6,8-dimethoxy-1-[(6-methoxy)pyridin-3-yl]-4-methyl-2,3-dihydro-1H-pyrrolo[3,2-c]quinoline;
1-(benzodioxol-5-ylmethyl)-6,8-dimethoxy-4-methyl-2,3-dihydro-1H-pyrrolo[3,2-c]quinoline;
6,8-dimethoxy-4-methyl-1-(3-methylbutyl)-2,3-dihydro-1H-pyrrolo[3,2-c]-quinoline;
1-cyclopropylmethyl-6,8-dimethoxy-4-methyl-2,3-dihydro-1H-pyrrolo[3,2-c]quinoline;
4-methyl-8-(morpholin-4-yl)-1-(4-phenoxyphenyl)-2,3-dihydro-1H-pyrrolo[3,2-c]quinoline;
8-methoxy-4-methyl-1-(1,2,3,4-tetrahydronaphthalen-1-yl)-2,3-dihydro-1H-pyrrolo[3,2-c]quinoline;
4-methyl-1-(2-phenylethyl)-2,3-dihydro-1H-pyrrolo[3,2-c]quinoline;
4,6-dimethyl-1-(2-methylphenyl)-2,3-dihydro-1H-pyrrolo[3,2-c]quinoline;
4,6-dimethyl-1-(2-phenylethyl)-2,3-dihydro-1H-pyrrolo[3,2-c]quinoline;
4-methyl-8-(piperidin-1-yl)-1-[4-(piperidin-1-yl)phenyl]-2,3-dihydro-1H-pyrrolo[3,2-c]quinoline;
4-methyl-8-(piperidin-1-yl)-1-(3-phenoxyphenyl)-2,3-dihydro-1H-pyrrolo[3,2-c]quinoline;
1-{4-[2-(N,N-dimethylamino)ethoxy]phenyl}-4-methyl-8-phenoxy-2,3-dihydro-1H-pyrrolo[3,2-c]quinoline;
1-[4-(4-fluorophenoxy)phenyl]-8-methoxy-4-methyl-2,3-dihydro-1H-pyrrolo[3,2-c]quinoline;
1-(benzodioxan-2-ylmethyl)-8-methoxy-4-methyl-2,3-dihydro-1H-pyrrolo[3,2-c]quinoline;
1-cyclohexyl-8-methoxy-4-methyl-2,3-dihydro-1H-pyrrolo[3,2-c]quinoline;
8-methoxy-4-methyl-1-phenyl-2,3-dihydro-1H-pyrrolo[3,2-c]quinoline;
4-methyl-8-phenoxy-1-[4-(3-pyridyl)phenyl]-2,3-dihydro-1H-pyrrolo[3,2-c]-quinoline;
4-methyl-8-phenoxy-1-[2-(3-pyridyl)ethyl]-2,3-dihydro-1H-pyrrolo[3,2-c]-quinoline;
4-methyl-8-phenoxy-1-(2-pyridylmethyl)-2,3-dihydro-1H-pyrrolo[3,2-c]-quinoline;
4-methyl-1-(5-methylpyrazin-2-ylmethyl)-8-phenoxy-2,3-dihydro-1H-pyrrolo[3,2-c]quinoline;
8-chloro-4-methyl-1-(2-phenylethyl)-2,3-dihydro-1H-pyrrolo[3,2-c]-quinoline;
4-methyl-1-(2-phenylethyl)-2,3-dihydro-1H-pyrrolo[3,2-c]quinoline-8-carboxylate;
4-methyl-8-(morpholin-1-yl)-1-(2-phenylethyl)-2,3-dihydro-1H-pyrrolo[3,2-c]quinoline;
ethyl [4-methyl-1-(2-phenylethyl)-2,3-dihydro-1H-pyrrolo[3,2-c]quinoline-8-yl]acetate;
1-[3-(4-methyl-8-phenoxy-2,3-dihydro-1H-pyrrolo[3,2-c]quinolin-1-yl)propyl]-pyrrolidin-2-one;
4-methyl-8-phenoxy-1-[2-(2-pyridyl)ethyl]-2,3-dihydro-1H-pyrrolo[3,2-c]quinoline;
ethyl 3-(8-methoxy-4-methyl-2,3-dihydro-1H-pyrrolo[3,2-c]quinoline-1-yl)propionate;
ethyl 4-(4-methyl-8-phenoxy-2,3-dihydro-1H-pyrrolo[3,2-c]quinoline-1-yl)butanoate;
methyl 4-(4-methyl-8-phenoxy-2,3-dihydro-1H-pyrrolo[3,2-c]quinoline-1-yl)butanoate;
ethyl (4-methyl-8-phenoxy-2,3-dihydro-1H-pyrrolo[3,2-c]quinoline-1-yl)acetate;
4-methyl-1-(1-methylpiperidin-4-yl)-8-phenoxy-2,3-dihydro-1H-pyrrolo[3,2-c]quinoline;
1-(1-benzylpyrrolidin-3-yl)-8-methoxy-4-methyl-2,3-dihydro-1H-pyrrolo[3,2-c]quinoline;
methyl 3-(4-methyl-8-phenoxy-2,3-dihydro-1H-pyrrolo[3,2-c]quinoline-1-yl)propionate;
1-((S)-indan-1-yl)-4-methyl-8-phenoxy-2,3-dihydro-1H-pyrrolo[3,2-c]-quinoline;
1-((R)-indan-1-yl)-4-methyl-8-phenoxy-2,3-dihydro-1H-pyrrolo[3,2-c]-quinoline;
1-(3-methoxypropyl)-4-methyl-8-phenoxy-2,3-dihydro-1H-pyrrolo[3,2-c]-quinoline;
4-methyl-8-phenoxy-1-(tetrahydrofuran-2-ylmethyl)-2,3-dihydro-1H-pyrrolo[3,2-c]quinoline;
1-[2-(4-chlorophenyl)ethyl]-4-methyl-8-phenoxy-2,3-dihydro-1H-pyrrolo[3,2-c]quinoline;
1-[2-(4-methoxyphenyl)ethyl]-4-methyl-8-phenoxy-2,3-dihydro-1H-pyrrolo[3,2-c]quinoline;
4-methyl-8-phenoxy-1-(2-phenylpropyl)-2,3-dihydro-1H-pyrrolo[3,2-c]-quinoline;
8-cyano-4-methyl-1-(2-phenylethyl)-2,3-dihydro-1H-pyrrolo[3,2-c]quinoline;
8-hydroxy-4-methyl-1-(2-phenylethyl)-2,3-dihydro-1H-pyrrolo[3,2-c]-quinoline;
8-phenoxy-1-(2-phenylethyl)-2,3-dihydro-1H-pyrrolo[3,2-c]quinoline;
6,8-dimethoxy-1-(4-hydroxyphenyl)-4-methylpyrrolo[3,2-c]quinoline;
8-methoxy-4-methyl-1-[4-(4-methylpiperazin-1-yl)-3-fluorophenyl]-2,3-dihydro-1H-pyrrolo[3,2-c]quinoline;
4-methyl-8-phenylamino-1-(2-phenylethyl)-2,3-dihydro-1H-pyrrolo[3,2-c]-quinoline;
[4-methyl-1-(2-phenylethyl)-2,3-dihydro-1H-pyrrolo[2,3-c]quinoline-8-oyl]-piperidine;
6,8-dimethoxy-1-(4-iso-propylphenyl)-4-methyl-2,3-dihydro-1H-pyrrolo[3,2-c]quinoline;
6-methoxy-1-(4-phenoxyphenyl)-4-methyl-2,3-dihydro-1H-pyrrolo[3,2-c]quinoline;
6-methoxy-1-(4-iso-propylphenyl)-4-methyl-2,3-dihydro-1H-pyrrolo[3,2-c]quinoline;
6,8-dimethoxy-1-(4-phenoxyphenyl)-4-methyl-2,3-dihydro-1H-pyrrolo[3,2-c]quinoline;
4-methyl-8-phenoxy-1-(4-phenoxyphenyl)-2,3-dihydro-1H-pyrrolo[3,2-c]quinoline;
1-(4-iso-propylphenyl)-6-phenoxy-4-methyl-2,3-dihydro-1H-pyrrolo[3,2-c]quinoline; and
4,6-dimethyl-1-(4-methylphenyl)-2,3-dihydro-1H-pyrrolo[3,2-c]quinoline;
or a pharmaceutically acceptable derivative thereof.

Further preferred examples of antimicrobial agents for use in combination in accordance with the present invention include a compound selected from the group consisting of:
(1-methyl-1H-benzimidazol-2-yl)-(6-hydroxy-2-methylquinolin-4-yl)amine;
(1-methyl-1H-benzimidazol-2-yl)-(2-methyl-6-phenoxyquinolin-4-yl)amine;
(1-methyl-1H-benzimidazol-2-yl)-(6-chloro-2-methylquinolin-4-yl)amine;
(1-methyl-1H-benzimidazol-2-yl)-(6-cyano-2-methylquinolin-4-yl)amine;

(1-methyl-1H-benzimidazol-2-yl)-(6-benzyloxy-2-methylquinolin-4-yl)amine;
(1-methyl-1H-benzimidazol-2-yl)-(5,6-dichloro-2-methylquinolin-4-yl)amine;
(1-methyl-1H-benzimidazol-2-yl)-(7-chloro-2-methylquinolin-4-yl)amine hydrochloride;
(1-methyl-1H-benzimidazol-2-yl)-(6,8-dichloro-2-methylquinolin-4-yl)amine;
[6-(4-fluorophenoxy)-2-methylquinolin-4-yl]-(1-methyl-1H-benzimidazol-2-yl)amine;
(2-methyl-6-phenylaminoquinolin-4-yl)-(1-methyl-1H-benzimidazol-2-yl)amine;
(1H-benzimidazol-2-yl)-(2-methyl-6-phenoxyquinolin-4-yl)amine;
(benzoxazol-2-yl)-(2-methyl-6-phenoxyquinolin-4-yl)amine;
(1H-benzimidazol-2-yl)-(6-chloro-2-methylquinazolin-4-yl)amine;
[2-methyl-6-(pyrimidin-2-yloxy)quinolin-4-yl]-(1-methyl-1H-benzimidazol-2-yl)amine;
(1-methyl-1H-benzimidazol-2-yl)-[2-methyl-6-(4-methylpiperazin-1-yl)-quinolin-4-yl]amine; and
(1-methyl-1H-benzimidazol-2-yl)-(2-morpholin-4-yl-6-phenoxyquinolin-4-yl)amine;
or a pharmaceutically acceptable derivative thereof.

Still further preferred examples of antimicrobial agents for use in combination in accordance with the present invention include a compound selected from the group consisting of:
6-chloro-2-methyl-4-(3-phenylpyrrolidin-1-yl)quinoline;
6-benzyloxy-2-methyl-4-(3-phenylpyrrolidin-1-yl)quinoline;
2-methyl-4-(3-phenylpyrrolidin-1-yl)-6-(pyridin-3-ylmethoxy)quinoline;
6-(4-methanesulfonylbenzyloxy)-2-methyl-4-(3-phenylpyrrolidin-1-yl)quinoline;
6-(4-methoxybenzyloxy)-2-methyl-4-(3-phenylpyrrolidin-1-yl)quinoline
2-methyl-6-phenethyloxy-4-(3-phenylpyrrolidin-1-yl)quinoline;
2-methyl-6-(5-methylisoxazol-3-ylmethoxy)-4-(3-phenylpyrrolidin-1-yl)quinoline;
4-(3-benzylpyrrolidin-1-yl)-2-methyl-6-phenoxyquinoline;
4-[3-(4-methoxyphenyl)pyrrolidin-1-yl]-2-methyl-6-phenoxyquinoline;
4-[3-(4-chlorophenyl)pyrrolidin-1-yl]-2-methyl-6-phenoxyquinoline;
[1-(2-methyl-6-phenoxyquinolin-4-yl)-pyrrolidin-3-yl]phenylamine;
N-[2-methyl-4-(3-phenylpyrrolidin-1-yl)quinolin-6-yl]benzamide;
N-[2-methyl-4-(3-phenylpyrrolidin-1-yl)-quinolin-6-yl]-2-phenylacetamide;
4-chloro-N-[2-methyl-4-(3-phenylpyrrolidin-1-yl)quinolin-6-yl]benzamide;
4-methoxy-N-[2-methyl-4-(3-phenylpyrrolidin-1-yl)quinolin-6-yl]benzamide;
2-methyl-N-[2-methyl-4-(3-phenylpyrrolidin-1-yl)quinolin-6-yl]benzamide;
pyrazine-2-carboxylic acid [2-methyl-4-(3-phenylpyrrolidin-1-yl)quinolin-6-yl]amide;
1H-pyrazole-4-carboxylic acid [2-methyl-4-(3-phenylpyrrolidin-1-yl)quinolin-6-yl]amide;
furan-2-carboxylic acid [2-methyl-4-(3-phenylpyrrolidin-1-yl)quinolin-6-yl]amide;
N-[2-methyl-4-(3-phenylpyrrolidin-1-yl)quinolin-6-yl]nicotinamide;
3-methyl-3H-imidazole-4-carboxylic acid [2-methyl-4-(3-phenylpyrrolidin-1-yl)quinolin-6-yl]amide;
5-methyl-1H-pyrazole-3-carboxylic acid [2-methyl-4-(3-phenylpyrrolidin-1-yl)-quinolin-6-yl]amide;
pyridazine-4-carboxylic acid [2-methyl-4-(3-phenylpyrrolidin-1-yl)-quinolin-6-yl]amide;
2-(4-methoxyphenyl)-N-[2-methyl-4-(3-phenylpyrrolidin-1-yl)quinolin-6-yl]acetamide;
2-(4-chlorophenyl)-N-[2-methyl-4-(3-phenylpyrrolidin-1-yl)quinolin-6-yl]acetamide;
3,5-dimethyl-isoxazole-4-carboxylic acid [2-methyl-4-(3-phenylpyrrolidin-1-yl)quinolin-6-yl]amide;
2-(3-methyl-isoxazol-5-yl)-N-[2-methyl-4-(3-phenyl-pyrrolidin-1-yl)-quinolin-6-yl]-acetamide;
N-[2-methyl-4-(3-phenylpyrrolidin-1-yl)quinolin-6-yl]benzenesulfonamide;
benzyl-[2-methyl-4-(3-phenylpyrrolidin-1-yl)quinolin-6-yl]amine;
(R- or S-)Benzyl-[2-methyl-4-(3-phenylpyrrolidin-1-yl)quinolin-6-yl]amine;
(S- or R-)Benzyl-[2-methyl-4-(3-phenylpyrrolidin-1-yl)quinolin-6-yl]amine;
(4-methoxybenzyl)-[2-methyl-4-(3-phenylpyrrolidin-1-yl)quinolin-6-yl]amine;
4-{[2-methyl-4-(3-phenylpyrrolidin-1-yl)quinolin-6-ylamino]methyl}benzonitrile;
1-[2-methyl-4-(3-phenylpyrrolidin-1-yl)quinolin-6-yl]pyrrolidin-2-one;
N-[2-methyl-4-(3-phenylpyrrolidin-1-yl)quinolin-6-yl]-3-phenyl propionamide;
5-methyl-isoxazole-3-carboxylic acid [2-methyl-4-(3-phenylpyrrolidin-1-yl)-quinolin-6-yl]amide;
pyridine-2-carboxylic acid [2-methyl-4-(3-phenylpyrrolidin-1-yl)quinolin-6-yl]amide;
N-[4-(3-benzylpyrrolidin-1-yl)-2-methylquinolin-6-yl]benzamide; and
2-methyl-6-phenoxy-4-(3-phenylpyrrolidin-1-yl)quinoline; or
or a pharmaceutically acceptable derivative thereof.

Particularly preferred antimicrobial agents for use combination in accordance with the present invention are 4-methyl-1-(2-phenylethyl)-8-phenoxy-2,3-dihydro-1H-pyrrolo[3,2-c]-quinoline (Example 9, WO2007054693), 4-(3-benzylpyrrolidin-1-yl)-2-methyl-6-phenoxyquinoline (Example 8, WO2008142384), and N-[4-(3-benzylpyrrolidin-1-yl)-2-methylquinolin-6-yl]benzamide (Example 38, WO2008142384), and pharmaceutically acceptable derivatives thereof. In one embodiment of the invention the antimicrobial agent is 4-(3-benzylpyrrolidin-1-yl)-2-methyl-6-phenoxyquinoline, N-[4-(3-benzylpyrrolidin-1-yl)-2-methylquinolin-6-yl]benzamide or a pharmaceutically acceptable derivative thereof. A more preferred antimicrobial agent is 4-methyl-1-(2-phenylethyl)-8-phenoxy-2,3-dihydro-1H-pyrrolo[3,2-c]-quinoline or a pharmaceutically acceptable derivative thereof such as the hydrochloride salt thereof.

When used in combination, compounds may be administered simultaneously, separately or sequentially. When administration is simultaneous, the compounds may be administered either in the same or a different pharmaceutical composition. Adjunctive therapy, i.e. where one agent is used as a primary treatment and the other agent is used to assist that primary treatment, is also an embodiment of the present invention.

According to a further embodiment of the invention, there is provided a product comprising one or more compounds selected from the following classes of biologically active agents: α-adrenergic antagonist, an anthelmintic agent, an antifungal agent, an antimalarial agent, an antineoplastic agent, an antipsychotic agent, an antioxidant, a vasodilator and/or a vitamin, or a pharmaceutically acceptable derivative thereof, and optionally an antimicrobial agent, as a combined preparation for simultaneous, separate or sequential use in the treatment of a microbial infection.

As used herein the term "pharmaceutically acceptable derivative" means:
(a) pharmaceutically acceptable salts with either acids or bases (e.g. acid addition salts); and/or
(b) solvates (including hydrates).

Acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalenesulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral or topical administration.

The formulations may conveniently be presented in unit dosage form and may be prepared by any of the methods well known in the art of pharmacy e.g. as described in "Remington: The Science and Practice of Pharmacy", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci, Streptococci, Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

Particular fungal conditions that may be treated by topical pharmaceutical compositions of the present invention also include include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea *versicolor*; and infections with *Trichophyton, Microsporum, Epidermophyton* or *Pityrosporum ovale* fungi.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combination of the invention by means of a single patient pack, or patients packs of each composition, including a package insert directing the patient to the correct use of the invention is a desirable feature of this invention.

According to a further embodiment of the present invention there is provided a patient pack comprising at least one compound selected from the group consisting of: an α-adrenergic antagonist, an anthelmintic agent, an antifungal agent, an antimalarial agent, an antineoplastic agent, an antipsychotic agent, an antioxidant, a vasodilator and/or a vitamin, or a pharmaceutically acceptable derivative thereof, and optionally an antimicrobial agent, and an information insert containing directions on the use of the invention.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationary phase;

(2) treating the stationary phase culture with one or more antimicrobial agents at a concentration and or time sufficient to kill growing bacteria, thereby selecting a phenotypically resistant sub-population;

(3) incubating a sample of the phenotypically resistant subpopulation with one or more test compounds or agents; and (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

Methods

Bacterial Strains

Staphylococcus aureus (Oxford strain); Gram positive; Reference strain.

Escherichia coli K12; Gram negative; Reference strain.

Pseudomonas aeruginosa NCTC 6751; Gram negative; Reference strain.

Growth of Bacteria

Bacteria were grown in 10 ml of nutrient broth (No. 2 (Oxoid)) overnight at 37° C., with continuous shaking at 120 rpm. The overnight cultures were diluted (1000×) in 100 ml of growth medium and then incubated without shaking for 10 days. Viability of the bacteria was estimated by colony forming unit (CFU) counts at 2 hour intervals at the first 24 hours and at 12-24 hours afterwards. From serial 10-fold dilutions of the experimental cultures, 100 µl samples were added to triplicate plates of nutrient agar plates (Oxoid) and blood agar plates (Oxoid). Colony forming units (CFU) were counted after incubation of the plates at 37° C. for 24 hours.

Log Phase Cultures

The above-described overnight cultures were diluted (1000×) with iso-sensitest broth. The cultures were then incubated at 37° C. with shaking for 1-2 hours to reach log CFU 6, which served as log phase cultures.

Stationary Phase Cultures

Cultures incubated for more than 24 hours are in the stationary phase. For drug screening, 5-6 day old stationary phase cultures were used.

Measurements of Bactericidal Activity Against Log Phase Cultures

The bactericidal activity of the drugs against log phase cultures were determined by minimal inhibitory concentration (MIC) of the drugs, which is defined as the lowest concentration which inhibits visible growth. Different concentrations of each test compound were incubated with the log-phase cultures in 96 well plates for 24 hours. Bactericidal activity was then examined by taking a spectrophotometer reading (using a plate reader) at 405 nm.

Measurements of Bactericidal Activity Against Stationary Phase Cultures

Different concentrations of each test compound were incubated with stationary phase cultures (5-6 day cultures) in 96 well plates for 24 or 48 hours. Bactericidal activity was then determined by taking CFU counts of the resulting cultures, as described above.

Measurements of Bactericidal Activity Against Persistent (Clinically Latent) Bacteria An antibiotic (gentamicin) was added to 5-6 day stationary-phase cultures to the final concentration of 50 to 100 µg/ml for 24 hours. After 24 hours of antibiotic treatment, the cells are washed 3 times with phosphate buffered saline (PBS), and then resuspended in PBS. The surviving bacterial cells are used as persisters. Viability is estimated by CFU counts. The persisters were then used in measurements of bactericidal activity for test compounds.

Different concentrations of each test compound were incubated with the (persister) cell suspension in 96 well plates for various periods of time (24 and 48 hours). Bactericidal activity was then determined by taking CFU counts of the resulting cultures, as described above.

EXAMPLES

Example 1

Bactericidal Activities of Compounds Against Stationary Phase S. aureus

The results obtained are summarised in Table 1 below.

TABLE 1

| | Log Kill µg/ml | | |
|---|---|---|---|
| Compound | 25 | 12.5 | 6.25 |
| Pyrvinium pamoate | 6.03 | 6.03 | 6.03 |
| Pararosaniline pamoate | 6.15 | 6.15 | 6.15 |
| Bithionate sodium | 6.15 | 6.15 | 0.01 |
| Phenylmercuric acetate | 6.03 | 6.03 | 6.03 |
| Tioconazole | 6.15 | 6.15 | 0.00 |
| Mefloquine | 6.03 | 6.03 | −0.01 |
| Mitomycin C | 6.15 | 6.15 | 6.15 |
| Toremifene citrate | 6.15 | 6.15 | 6.15 |
| Sanguinarine sulfate | 6.15 | 6.15 | 6.15 |
| Carboplatin | 6.03 | 6.03 | 0.92 |
| Cisplatin | 6.03 | 6.03 | 6.03 |
| Hydroquinone | 6.15 | 6.15 | 6.15 |
| Thioridazine hydrochloride | 6.03 | 6.03 | 6.03 |
| Trifluoperazine hydrochloride | 6.03 | 2.22 | 0.00 |
| Triflupromazine hydrochloride | 6.15 | 6.15 | 6.15 |
| Chlorprothixene hydrochloride | 6.15 | 6.15 | 1.83 |
| Perhexiline maleate | 6.15 | 6.15 | 6.15 |
| Suloctidil | 6.03 | 6.03 | 6.03 |
| Nisoldipine | 6.15 | 6.15 | 0.00 |

Conclusions

All compounds exhibited significant bactericidal activities against stationary phase S. aureus. There were 6 log of bacteria incubated with the compounds. Complete kill was observed at 25, 2.5 µg/ml, and in some cases at 6.25 ug/ml.

Example 2

Bactericidal Activities of Compounds Against Loci Phase and Stationary Phase E. coli The results obtained are summarised in Tables 2 and 3 below.

TABLE 2

| | Log kill µg/ml | | |
|---|---|---|---|
| Compound | 25.00 | 12.50 | 6.25 |
| Quinacrine hydrochloride | 6.14 | 2.14 | 1.27 |
| Pararosaniline pamoate | 6.14 | 6.14 | 1.90 |
| Phenylmercuric acetate | 6.14 | 6.14 | 6.14 |
| Acrisorcin | 6.14 | 6.14 | 6.14 |
| Mefloquine | 6.14 | 6.14 | 2.48 |
| Mitomycin C | 6.14 | 6.14 | 2.27 |
| Mitoxanthrone hydrochloride | 6.14 | 6.14 | 6.14 |
| Bleomycin | 6.14 | 6.14 | 2.22 |
| Doxorubicin | 6.14 | 6.14 | 6.14 |
| Sanguinarine sulfate | 6.14 | 2.40 | −0.10 |

TABLE 2-continued

| | Log kill µg/ml | | |
|---|---|---|---|
| Compound | 25.00 | 12.50 | 6.25 |
| Carboplatin | 6.14 | 6.14 | 6.14 |
| Cisplatin | 6.14 | 6.14 | 6.14 |
| Hydroquinone | 6.14 | 6.14 | 6.14 |
| Thioridazine hydrochloride | 6.14 | 6.14 | 6.14 |
| Trifluoperazine hydrochloride | 6.14 | 6.14 | −0.12 |
| Triflupromazine hydrochloride | 6.14 | 6.14 | 2.10 |

TABLE 3

| Compound | E. coli MIC µg/ml |
|---|---|
| Quinacrine hydrochloride | — |
| Pararosaniline pamoate | 10 |
| Bithionate sodium | 5 |
| Phenylmercuric acetate | 0.15 |
| Acrisorcin | — |
| Mefloquine | 10 |
| Mitomycin C | 0.3 |
| Mitoxanthrone hydrochloride | — |
| Bleomycin | 0.15 |
| Doxorubicin | — |
| Sanguinarine sulfate | — |
| Carboplatin | — |
| Cisplatin | — |
| Hydroquinone | — |
| Thioridazine hydrochloride | 10 |
| Trifluoperazine hydrochloride | 20 |
| Triflupromazine hydrochloride | 10 |
| Chlorprothixene hydrochloride | 20 |
| Perhexiline maleate | 10 |
| Suloctidil | 10 |
| Nisoldipine | — |
| Vitamin B12 | — |

Key: — signifies MIC higher than 50 µg/ml

Conclusions

All compounds exhibited significant bactericidal activities against stationary phase E. coli. There were 6 log of bacteria incubated with the compounds. Complete kill was observed at 25, 12.5 µg/ml, and and in some cases 6.25 ug/ml.

Certain compounds were also were active against log phase E. coli showing MIC between 0.15 to 20 µg/ml.

Example 3

Bactericidal Activity of Suloctidil and Mefloquine Against Stationary Phase P. aeruginosa The results obtained are summarised in FIG. 1.

Conclusions

Mefloquine was active against stationary phase P. aeruginosa. At 80 µg/ml, mefloquine removed more than $10^7$ of the organism. There was about 1.5 log reduction of the bacterium at 40 µg/ml. Suloctidil displayed no observable activity against stationary phase P. aeruginosa.

Example 4

Bactericidal Activities of Compounds Against Persistent E. coli

The results obtained are summarised in Table 4 below.

TABLE 4

| | Log Kill µg/ml | | |
|---|---|---|---|
| Compounds | 25 | 12.5 | 6.25 |
| Bithionate sodium | 6.21 | 0.03 | 0.01 |
| Bleomycin | 6.21 | 6.21 | 1.55 |
| Carboplatin | 6.21 | 2.55 | 1.55 |
| Chlorprothixene hydrochloride | 6.21 | 0.03 | 0.02 |
| Cisplatin | 6.21 | 6.21 | 6.21 |
| Vitamin B12 | 6.21 | 6.21 | 0.03 |
| Mefloquine | 6.21 | 0.03 | 0.02 |
| Mitomycin C | 6.21 | 6.21 | 6.21 |
| Mitoxanthrone hydrochloride | 6.21 | 6.21 | 6.21 |
| Pararosaniline pamoate | 6.21 | 0.01 | −0.01 |
| Perhexiline maleate | 6.21 | 0.04 | −0.01 |
| Phenylmercuric acetate | 6.21 | 6.21 | 6.21 |
| Sanguinarine sulfate | 6.21 | 1.47 | 0.04 |
| Suloctidil | 6.21 | 0.02 | 0.02 |
| Thioridazine hydrochloride | 6.21 | 0.03 | 0.04 |
| Triflupromazine hydrochloride | 6.21 | 2.34 | 0.03 |

Conclusions

All compounds exhibited significant bactericidal activities against persistent E. coli selected by treatment with getamicin. There were 6 log of bacteria incubated with the compounds. Complete kill was observed at 25 µg/ml and in some cases at 12.5 and 6.25 µg/ml.

Example 5

In vitro Activity of of Phenoxybenzamine Hydrochloride (HT00800157) with Polymyxin E Against Log Phase E. coli by Chequerboard Analysis The results obtained are summarised in Table 5 below.

TABLE 5

| | | POLYMYXIN E µg/ml | | | | | | | | | | | |
|---|---|---|---|---|---|---|---|---|---|---|---|---|---|
| | | 2 | 1 | 0.5 | 0.25 | 0.125 | 0.0625 | 0.03125 | 0.015625 | 0.0078 | 0.0039 | 0.0019 | 0 |
| HT00800157 µg/ml | 64 | 0.48 | 0.48 | 0.47 | 0.47 | 0.46 | 0.47 | 0.48 | 1.45 | 1.44 | 1.47 | 1.57 | 1.60 |
| | 32 | 0.50 | 0.50 | 0.51 | 0.51 | 0.51 | 1.27 | 1.52 | 1.52 | 1.53 | 1.51 | 1.49 | 1.57 |
| | 16 | 0.51 | 0.52 | 0.52 | 0.52 | 0.52 | 1.48 | 1.55 | 1.57 | 1.55 | 1.55 | 1.51 | 1.56 |
| | 8 | 0.50 | 0.51 | 0.51 | 0.52 | 1.51 | 1.54 | 1.57 | 1.56 | 1.58 | 1.55 | 1.57 | 1.56 |
| | 4 | 0.51 | 0.52 | 0.52 | 0.52 | 1.48 | 1.57 | 1.60 | 1.60 | 1.60 | 1.56 | 1.61 | 1.60 |
| | 2 | 0.49 | 0.50 | 0.49 | 0.49 | 1.25 | 1.46 | 1.45 | 1.57 | 1.49 | 1.48 | 1.45 | 1.53 |
| | 1 | 0.50 | 0.51 | 0.51 | 0.50 | 1.60 | 1.54 | 1.53 | 1.52 | 1.56 | 1.52 | 1.54 | 1.52 |
| | 0 | 0.50 | 0.49 | 0.49 | 1.25 | 1.48 | 1.52 | 1.42 | 1.53 | 1.55 | 1.55 | 1.53 | 1.53 |

Conclusions
1. MIC for phenoxybenzamine hydrochloride alone was >64 μg/ml.
2. In combination with polymyxin E at 0.06 μg/ml, MIC for phenoxybenzamine hydrochloride was 64 μg/ml.
3. In combination with polymyxin E at 0.25 μg/ml, the MIC for phenoxybenzamine hydrochloride was reduced to 1 μg/ml.

Example 6

In vitro Activity of Mefloquine with Polymyxin E (Colistin) NDM-1 *Klebsiella pneumoniae*

Chequerboard Analysis

The results obtained from chequerboard analysis are summarised in Table 6 below.

TABLE 6

| | | Mefloquine | | | | | | | | | | | |
|---|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.35 | 0.33 | 0.34 | 0.33 | 0.33 | 0.33 | 0.34 | 0.33 | 0.33 | 0.34 | 0.34 | 0.33 |
| | 16 | 0.33 | 0.33 | 0.34 | 0.34 | 0.33 | 0.33 | 0.35 | 0.34 | 0.67 | 0.68 | 0.68 | 0.78 |
| | 8 | 0.33 | 0.34 | 0.34 | 0.34 | 0.34 | 0.34 | 0.34 | 0.61 | 0.44 | 0.35 | 0.45 | 0.82 |
| | 4 | 0.34 | 0.34 | 0.33 | 0.34 | 0.34 | 0.35 | 0.69 | 0.62 | 0.74 | 0.74 | 0.81 | 0.34 |
| | 2 | 0.34 | 0.33 | 0.34 | 0.34 | 0.35 | 0.68 | 0.82 | 0.92 | 0.92 | 0.91 | 0.94 | 1.05 |
| | 1 | 0.33 | 0.34 | 0.34 | 0.35 | 0.72 | 0.97 | 0.98 | 0.96 | 0.95 | 0.97 | 0.95 | 1.03 |
| | 0.5 | 0.34 | 0.33 | 0.34 | 0.67 | 1.00 | 1.04 | 1.05 | 1.00 | 1.04 | 1.08 | 1.06 | 1.08 |
| | 0 | 0.34 | 0.33 | 0.60 | 0.82 | 1.10 | 1.15 | 1.09 | 1.09 | 1.10 | 1.08 | 1.10 | 1.19 |

Synergy in the context of antimicrobials drugs is measured in a number of ways that conform to the generally accepted opinion that "synergy" is an effect greater than additive. One of the ways to assess whether synergy has been observed is to use the "chequerboard" technique which leads to the generation of a value called the fractional inhibitory concentration index (FICI).

Orhan et al J. Clin. Microbiol. 2005, 43(1):140 describes the chequerboard method and analysis in the paragraph bridging pages 140-141, and explains that the FICI value is a ratio of the sum of the MIC (Minimum Inhibitory Concentration) level of each individual component alone and in the mixture.

The combination is considered synergistic when the ΣFIC is <0.5, indifferent when the ΣFIC is >0.5 to <2, and antagonistic when the ΣFIC is >2.

Conclusions
1. FIC index=0.031 showing synergy between mefloquine and colistin.
2. Colistin MIC reduced from 32 mg/L to 0.5 mg/L when combined with 64 mg/L of mefloquine.

Time Kill Curves

Another accepted test for ascertaining the presence or absence of synergy is to use time-kill methods where the dynamic effect of a drug combination is compared to each drug alone when assessing the effect on bacterial log or stationary-growth over time. Again, the possible results are for synergistic, additive or antagonistic effects.

The following time kill curves, FIGS. 2-7, demonstrate the synergy observed between colistin and mefloquine against NDM-1 *Klebsiella pneumoniae*.

Example 7

In vitro Activity of Suloctidil and Colistin Against NDM-1 *Klebsiella pneumoniae*

Chequerboard Analysis

The results obtained from chequerboard analysis are summarised in Table 7 below.

TABLE 7

| | | Suloctidil | | | | | | | | | | | |
|---|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.39 | 0.38 | 0.36 | 0.36 | 0.35 | 0.36 | 0.36 | 0.36 | 0.36 | 0.35 | 0.36 | 0.36 |
| | 16 | 0.39 | 0.38 | 0.37 | 0.36 | 0.36 | 0.36 | 0.36 | 0.36 | 0.53 | 0.36 | 0.46 | 0.53 |
| | 8 | 0.42 | 0.38 | 0.36 | 0.35 | 0.36 | 0.36 | 0.36 | 0.37 | 0.54 | 0.41 | 0.51 | 0.44 |
| | 4 | 0.42 | 0.36 | 0.37 | 0.36 | 0.36 | 0.36 | 0.36 | 0.49 | 0.68 | 0.66 | 0.78 | 0.87 |
| | 2 | 0.41 | 0.37 | 0.37 | 0.36 | 0.36 | 0.63 | 0.62 | 0.67 | 0.80 | 0.80 | 0.78 | 0.95 |
| | 1 | 0.37 | 0.37 | 0.36 | 0.37 | 0.55 | 0.63 | 0.74 | 0.92 | 0.86 | 0.84 | 0.83 | 1.02 |
| | 0.5 | 0.37 | 0.36 | 0.37 | 0.53 | 0.57 | 0.68 | 0.81 | 0.85 | 0.89 | 0.82 | 0.95 | 0.98 |
| | 0 | 0.61 | 0.44 | 0.38 | 0.60 | 0.60 | 0.70 | 0.94 | 0.93 | 0.98 | 1.03 | 0.97 | 1.03 |

Conclusion:
1. FIC index=0.094 showing synergy between suloctidil and colistin.
2. Colistin MIC reduced from 16 mg/L to 1 mg/L when combined with 32 mg/L of suloctidil.

Time Kill Curves

The following time kill curves, FIGS. 8-11, demonstrate the synergy observed between colistin and suloctidil against NDM-1 *Klebsiella pneumoniae*.

Example 8

In vitro Activity of Thioridazine Hydrochloride and Colistin Against NDM-1 *Klebsiella pneumoniae*

Chequerboard Analysis

The results obtained from chequerboard analysis are summarised in Table 8.

TABLE 8

| | | Thioridazine hydrochloride | | | | | | | | | | | |
|---|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.55 | 0.39 | 0.39 | 0.39 | 0.39 | 0.39 | 0.39 | 0.39 | 0.39 | 0.49 | 0.42 | 0.41 |
| | 16 | 0.54 | 0.39 | 0.39 | 0.39 | 0.39 | 0.39 | 0.39 | 0.39 | 0.39 | 0.39 | 0.39 | 0.39 |
| | 8 | 0.52 | 0.39 | 0.39 | 0.38 | 0.50 | 0.48 | 0.48 | 0.48 | 0.48 | 0.52 | 0.57 | 0.57 |
| | 4 | 0.53 | 0.39 | 0.39 | 0.40 | 0.46 | 0.46 | 0.41 | 0.55 | 0.47 | 0.54 | 0.55 | 0.54 |
| | 2 | 0.52 | 0.39 | 0.39 | 0.46 | 0.52 | 0.62 | 0.81 | 0.77 | 0.80 | 0.80 | 0.73 | 0.87 |
| | 1 | 0.53 | 0.40 | 0.39 | 0.60 | 0.77 | 0.73 | 0.74 | 0.86 | 0.80 | 0.77 | 0.82 | 0.94 |
| | 0.5 | 0.52 | 0.46 | 0.60 | 0.68 | 0.78 | 0.80 | 0.80 | 1.34 | 0.81 | 0.77 | 0.80 | 0.94 |
| | 0 | 1.41 | 0.76 | 0.73 | 0.93 | 0.96 | 0.96 | 0.96 | 0.96 | 0.97 | 0.97 | 0.98 | 1.03 |

Conclusion:
1. FIC index=0.16 showing synergistic activity between thioridazine hydrochloride and colistin.
2. Colistin MIC reduced from 16 mg/L to 0.5 mg/L when combined with 256 mg/L of thioridazine hydrochloride.

Time Kill Curve

Figure 12:
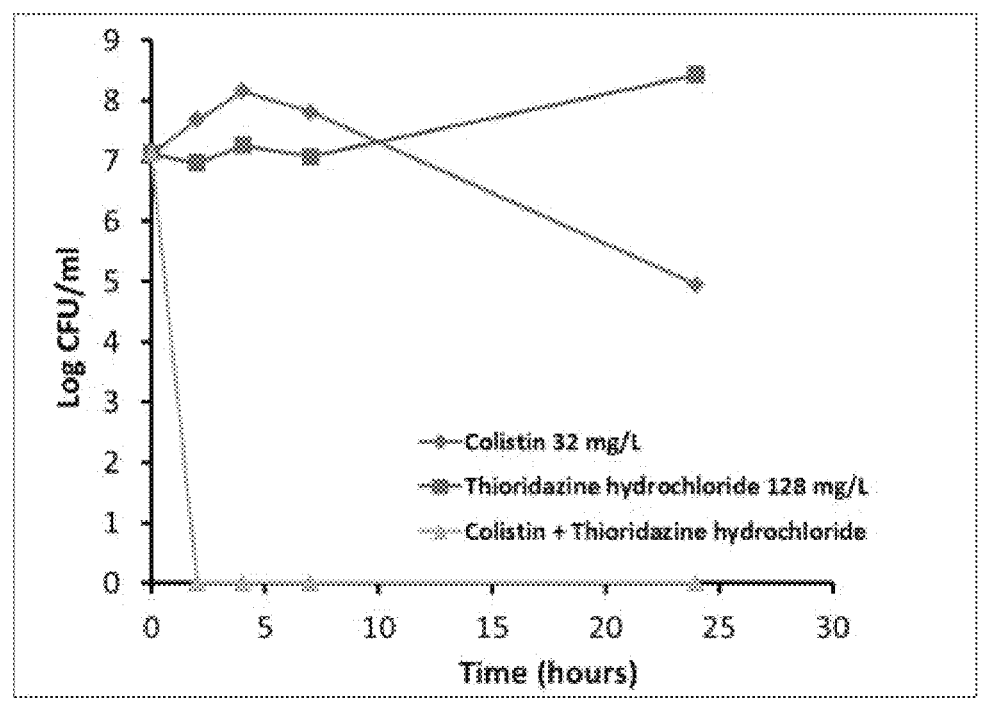

The following time kill curve, FIG. 12, demonstrates the synergy between thioridazine hydrochloride and colistin against NDM-1 *Klebsiella pneumoniae*.

Example 9

In vitro Activity of Chlorprothixene Hydrochloride and Colistin Against NDM-1 *Klebsiella pneumoniae*

Chequerboard Analysis

The results obtained from chequerboard analysis are summarised in Table 9.

TABLE 9

| | | Chlorprothixene hydrochloride | | | | | | | | | | | |
|---|---|---|---|---|---|---|---|---|---|---|---|---|---|
| | | 256 | 128 | 64 | 32 | 16 | 8 | 4 | 2 | 1 | 0.5 | 0.25 | 0 |
| Colistin | 32 | 0.40 | 0.40 | 0.40 | 0.39 | 0.39 | 0.65 | 0.65 | 0.52 | 0.40 | 0.59 | 0.39 | 0.39 |
| | 16 | 0.41 | 0.39 | 0.40 | 0.41 | 0.40 | 0.40 | 0.40 | 0.39 | 0.40 | 0.40 | 0.40 | 0.40 |
| | 8 | 0.40 | 0.40 | 0.40 | 0.41 | 0.59 | 0.67 | 0.47 | 0.76 | 0.76 | 0.72 | 0.72 | 0.68 |
| | 4 | 0.39 | 0.39 | 0.40 | 0.45 | 0.53 | 0.58 | 0.60 | 0.67 | 0.69 | 0.65 | 0.77 | 0.80 |
| | 2 | 0.40 | 0.39 | 0.40 | 0.46 | 0.77 | 0.81 | 0.87 | 0.83 | 0.87 | 0.81 | 0.90 | 1.07 |
| | 1 | 0.40 | 0.40 | 0.40 | 0.78 | 0.91 | 0.93 | 0.93 | 0.95 | 0.85 | 0.89 | 0.98 | 1.13 |
| | 0.5 | 0.40 | 0.39 | 0.62 | 0.81 | 0.90 | 0.94 | 0.94 | 0.94 | 0.97 | 0.95 | 0.94 | 1.12 |
| | 0 | 0.40 | 0.62 | 0.70 | 1.05 | 1.10 | 1.13 | 1.12 | 1.12 | 1.13 | 1.15 | 1.14 | 1.18 |

Conclusion:
1. FIC index=0.05 showing synergistic activity between chlorprothixene hydrochloride and colistin.
2. Colistin MIC reduced from 16 mg/L to 0.5 mg/L when combined with 128 mg/L of
   Chlorprothixene hydrochloride.

Time Kill Curve

Figure 13:
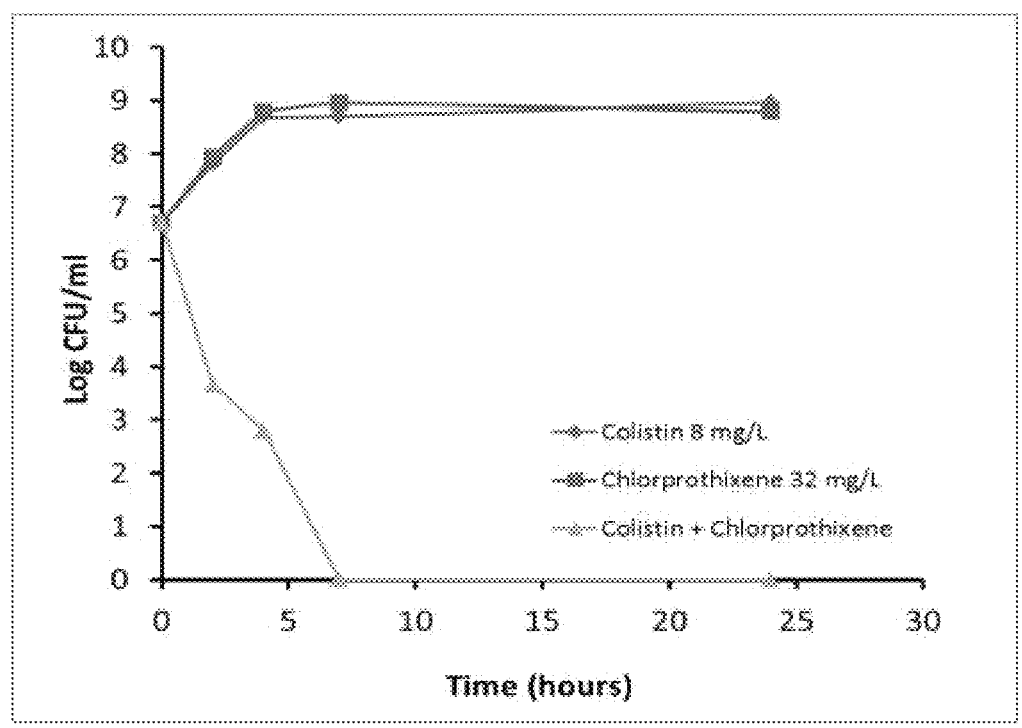

The following time kill curve, FIG. 13, demonstrates the synergy between chlorprothixene hydrochloride and colistin against NDM-1 *Klebsiella pneumoniae*.

Example 10

In Vitro Activity of Triflupromazine and Colistin Against NDM-1 *Klebsiella pneumoniae*

Chequerboard Analysis

The results obtained from chequerboard analysis are summarised in Table 10.

TABLE 10

|  |  | Triflupromazine | | | | | | | | | | | |
|---|---|---|---|---|---|---|---|---|---|---|---|---|---|
|  |  | 256 | 128 | 64 | 32 | 16 | 8 | 4 | 2 | 1 | 0.5 | 0.25 | 0 |
| Colistin | 32 | 0.40 | 0.40 | 0.40 | 0.40 | 0.40 | 0.40 | 0.40 | 0.40 | 0.40 | 0.40 | 0.40 | 0.40 |
|  | 16 | 0.57 | 0.43 | 0.40 | 0.51 | 0.40 | 0.40 | 0.39 | 0.40 | 0.43 | 0.40 | 0.50 | 0.69 |
|  | 8 | 0.40 | 0.40 | 0.40 | 0.49 | 0.40 | 0.46 | 0.46 | 0.60 | 0.67 | 0.63 | 0.62 | 0.63 |
|  | 4 | 0.40 | 0.40 | 0.40 | 0.56 | 0.63 | 0.75 | 0.65 | 0.77 | 0.70 | 0.68 | 0.86 | 0.89 |
|  | 2 | 0.40 | 0.39 | 0.40 | 0.58 | 0.79 | 0.83 | 0.85 | 0.86 | 0.83 | 0.88 | 0.94 | 1.09 |
|  | 1 | 0.40 | 0.40 | 0.48 | 0.78 | 0.86 | 0.86 | 0.87 | 0.89 | 0.86 | 0.90 | 0.99 | 1.12 |
|  | 0.5 | 0.40 | 0.39 | 0.58 | 0.83 | 0.90 | 0.93 | 0.94 | 0.94 | 0.95 | 0.98 | 0.97 | 1.14 |
|  | 0 | 0.41 | 0.76 | 0.73 | 1.08 | 1.11 | 1.17 | 1.14 | 1.13 | 1.14 | 1.13 | 1.11 | 1.15 |

Conclusion:
1. FIC index=0.02 showing synergistic activity for triflupromazine and colistin.
2. Colistin MIC reduced from 32 mg/L to 0.5 mg/L when combined with 128 mg/L of Triflupromazine.

Time Kill Curve

Figure 14:
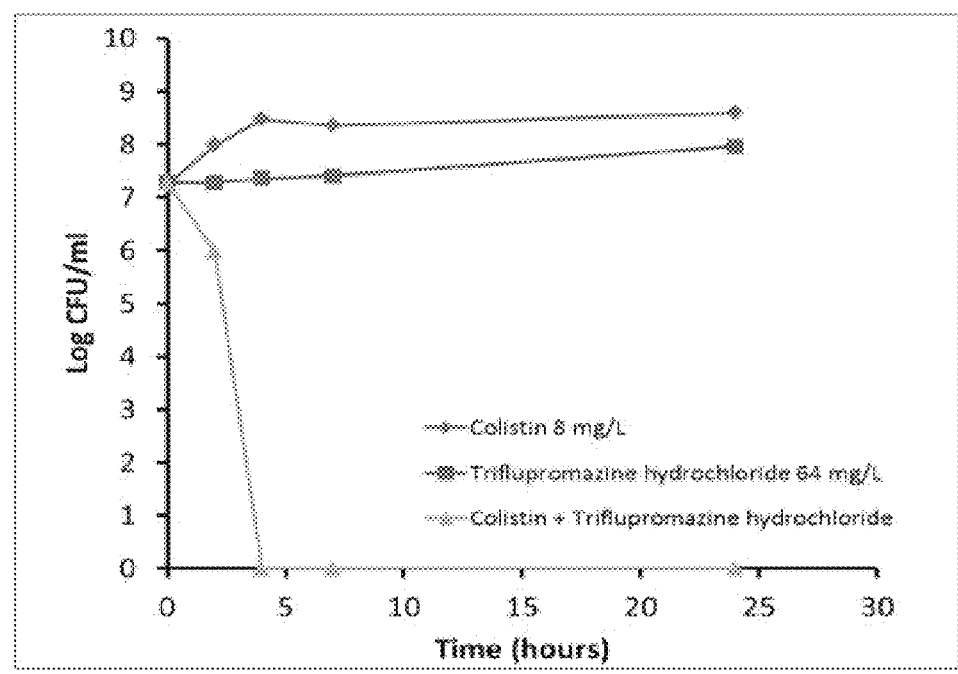

The following time kill curve, FIG. 14, demonstrates synergy between triflupromazine hydrochloride and colistin against NDM-1 *Klebsiella pneumoniae*.

Example 11

In vitro Activity of Trifluoperazine Hydrochloride and Colistin Against NDM-1 *Klebsiella pneumoniae*

Chequerboard Analysis

The results obtained from chequerboard analysis are summarised in Table 11 below.

TABLE 11

|  |  | Trifluoperazine hydrochloride | | | | | | | | | | | |
|---|---|---|---|---|---|---|---|---|---|---|---|---|---|
|  |  | 256 | 128 | 64 | 32 | 16 | 8 | 4 | 2 | 1 | 0.5 | 0.25 | 0 |
| Colistin | 32 | 0.63 | 0.39 | 0.39 | 0.39 | 0.46 | 0.39 | 0.43 | 0.49 | 0.39 | 0.39 | 0.39 | 0.41 |
|  | 16 | 0.61 | 0.39 | 0.39 | 0.39 | 0.39 | 0.39 | 0.40 | 0.47 | 0.42 | 0.40 | 0.40 | 0.48 |
|  | 8 | 0.60 | 0.39 | 0.39 | 0.39 | 0.46 | 0.50 | 0.57 | 0.41 | 0.52 | 0.52 | 0.52 | 0.53 |
|  | 4 | 0.59 | 0.40 | 0.39 | 0.40 | 0.43 | 0.52 | 0.42 | 0.46 | 0.77 | 0.82 | 0.74 | 0.90 |
|  | 2 | 0.58 | 0.39 | 0.39 | 0.39 | 0.41 | 0.47 | 0.46 | 0.83 | 0.85 | 0.86 | 0.78 | 0.91 |
|  | 1 | 0.57 | 0.40 | 0.40 | 0.48 | 0.76 | 0.73 | 0.74 | 0.81 | 0.83 | 0.74 | 0.81 | 0.93 |
|  | 0.5 | 0.56 | 0.40 | 0.38 | 0.78 | 0.80 | 0.75 | 0.79 | 0.83 | 0.82 | 0.80 | 0.83 | 0.96 |
|  | 0 | 1.33 | 0.87 | 0.77 | 0.95 | 0.98 | 0.97 | 0.95 | 0.96 | 0.94 | 0.95 | 0.96 | 1.00 |

Figure 15:
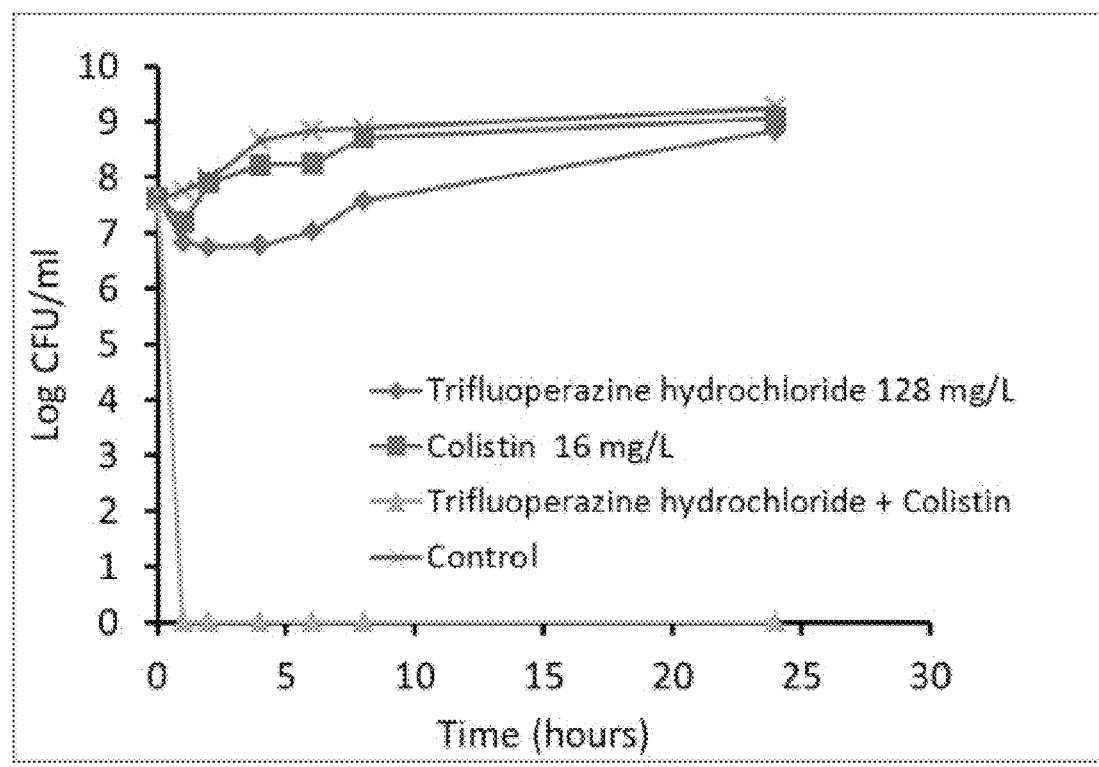

Conclusion:
1. FIC index=0.04 showing synergistic activity for trifluoperazine hydrochloride and colistin.
2. Colistin MIC reduced from 16 mg/L to 0.5 mg/L when combined with 256 mg/L of trifluoperazine hydrochloride Time Kill Curve The following time kill curve, FIG. 15, demonstrates the synergy between Trifluoperazine hydrochloride and colistin against NDM-1 *Klebsiella pneumoniae*.

The invention claimed is:

1. A synergistic combination comprising phenoxybenzamine, or a pharmaceutically acceptable salt and/or solvate thereof; and polymyxin E (colistin).

2. A synergistic combination according to claim 1, wherein the phenoxybenzamine is phenoxybenzamine hydrochloride.

3. A method of treating a microbial infection which comprises administering to a mammal, the synergistic combination according to claim 1.

4. A method of treating a microbial infection according to claim 3, wherein the infection is a bacterial infection.

5. A product comprising the synergistic combination of claim 1 for simultaneous, separate or sequential use in the treatment of a microbial infection.

6. A pharmaceutical composition comprising the synergistic combination of claim 1 and a pharmaceutically acceptable carrier.

* * * * *